United States Patent [19]
Marciani

[11] Patent Number: 6,080,725
[45] Date of Patent: *Jun. 27, 2000

[54] IMMUNOSTIMULATING AND VACCINE COMPOSITIONS EMPLOYING SAPONIN ANALOG ADJUVANTS AND USES THEREOF

[75] Inventor: Dante J. Marciani, Brimingham, Ala.

[73] Assignee: Galenica Pharmaceuticals, Inc., Frederick, Md.

[ * ] Notice: This patent is subject to a terminal disclaimer.

[21] Appl. No.: 09/290,606

[22] Filed: Apr. 13, 1999

Related U.S. Application Data

[63] Continuation-in-part of application No. 09/081,647, May 20, 1998, Pat. No. 5,977,081.

[60] Provisional application No. 60/047,129, May 20, 1997, and provisional application No. 60/080,389, Apr. 2, 1998.

[51] Int. Cl.$^7$ .......................... A61K 31/705; A61K 39/00
[52] U.S. Cl. .......................... 514/26; 424/184.1; 514/25; 536/4.1; 536/5
[58] Field of Search .......................... 424/184.1; 514/25, 514/26; 536/4.1, 5

[56] References Cited

U.S. PATENT DOCUMENTS

| | | | |
|---|---|---|---|
| 4,235,877 | 11/1980 | Fullerton | 424/89 |
| 5,057,540 | 10/1991 | Kensil et al. | 514/25 |
| 5,273,965 | 12/1993 | Kensil et al. | 514/3 |
| 5,443,829 | 8/1995 | Kensil et al. | 424/195.1 |
| 5,508,310 | 4/1996 | Rhodes | 514/576 |
| 5,583,112 | 12/1996 | Kensil et al. | 514/25 |
| 5,650,398 | 7/1997 | Kensil et al. | 514/25 |
| 5,750,110 | 5/1998 | Prieels et al. | 424/208.1 |
| 5,817,314 | 10/1998 | So et al. | 424/184.1 |
| 5,977,081 | 11/1999 | Marciani | 514/25 |

FOREIGN PATENT DOCUMENTS

| | | |
|---|---|---|
| 0 244 719 A2 | 11/1987 | European Pat. Off. . |
| WO 90/03184 | 4/1990 | WIPO . |
| WO 93/05789 | 4/1993 | WIPO . |

OTHER PUBLICATIONS

"Saponins" by K. Hostettmann and A. Marston. Cambridge University Press, pp. 326–329, 1995.

Akihisa, T., et al., "The 24α– and 24β–Epimers of 24–Ethylcholesta–5,22–dien–3β–ol in Two Clerodendrum Species," Phytochemistry 27:1169–1172, (1988).

ApSimon, J.W., et al., "Saponins from Marine Invertebrates," Studies in Organic Chemistry 17: Chemistry and Biotechnology Active of Biologically Natural Products, Proceedings of the Second International Conference, Budapest, Aug. 15–19, 1983, Szántay, C., Ed., Elsevier: Amsterdam, pp. 273–286 (1984).

Bohn, J.A., and BeMiller, J.N., "(1→3)–β–D–Glucans as biological response modifiers: a review of structure–functional activity relationships," Carbohydrate Polymers 28:3–14 (1995).

Bomford, R., et al., "Adjuvanticity and ISCOM formation by structurally diverse saponins," Vaccine 10:572–577 (1992).

Bowyer, P., et al., "Host Range of a Plant Pathogenic Fungus Determined by a Saponin Detoxifying Enzyme," Science 267:371–374 (1995).

Cleland, J.L., et al., "Isomerizatin and Formulation Stability of the Vaccine Adjuvant QS–21" J. Pharm. Sci. 85:22–28 (1996).

Cox, J.C., and Coulter, A.R., "Adjuvants—a classification and review of their modes of action," Vaccine 15:248–256 (Feb. 1997).

Dalsgaard, K., "A Study of the Isolation and Characterization of the Saponin Quil A," Acta Vet. Scand., 19 (Supp. 69):7–40 (1978).

Dalsgaard, K., "Saponin Adjuvants. III. Isolation of a Substance for Quillaja saponaria Molina with Adjuvant Activity in Foot–and Mouth Disease Vaccines," Archiv für die gesamte Virusforschung 44:243–254 (1974).

Higucchi, R., and Komori, T., "Structures of Compounds Derived from the Acyl Moieties of Quillajasaponin," Phytochemistry 26:2357–2360 (1987).

Higuchi, R., et al., "Structure of Desacylsaponins Obtained from the Bark of Quillaja Saponari," Phytochemistry 26:229–235 (1987).

Higuchi, R., et al., "Am Acylated Triterpenoid Saponin From Quillaja Saponaria," Phytochemistry 27:1165–1168 (1988).

Hostettmann, K., et al., "Saponins," Methods in Plant Biochemistry 7:435–471 (1991).

Johnson, H.E., et al., "Active Immunization of Heifers Against Luteinizing Hormone–Releasing Hormone, Human Chorionic Gonadotropin and Bovine Luteinizing Hormone," J. Anim. Sci. 66:719–726 (1988).

Kensil, C.R., et al., "Separation and Characterization of Saponins with Adjuvant Activity from Quillaja saponaria Molina Cortex," J. Immunol. 146:431–437 (1991).

(List continued on next page.)

Primary Examiner—Howard C. Lee
Attorney, Agent, or Firm—Sterne, Kessler, Goldstein & Fox, P.L.L.C.

[57] ABSTRACT

The present invention is directed to vaccines comprising (1) one or more bacterial, viral or tumor-associated antigens; and (2) one or more saponin-lipophile conjugate in which a lipophilic moiety such as a lipid, fatty acid, polyethylene glycol or terpene is covalently attached to a non-acylated or desacylated triterpene saponin via a carboxyl group present on the 3-O-glucuronic acid of the triterpene saponin. The attachment of a lipophile moiety to the 3-O-glucuronic acid of a saponin such as Quillaja desacylsaponin, lucyoside P, or saponin from Gypsophila, Saponaria and Acanthophyllum enhances their adjuvant effects on humoral and cell mediated immunity. Additionally, the attachment of a lipophile moiety to the 3-O-glucuronic acid residue of non- or desacylsaponin yields a saponin analog that is easier to purify, less toxic, chemically more stable, and possesses equal or better adjuvant properties than the original saponin.

37 Claims, 11 Drawing Sheets

OTHER PUBLICATIONS

Kensil, C.R., et al., "Structure/Function Studies on QS–21, a Unique Immunological Adjuvant from *Quillaja Saponaria,*" *Adv. Exp. Med. Biol.* 404:165–172 (1996).

Lacaille–Dubois, M.A., and Wagner, H., "A review of the biological and pharmacological activities of saponins," *Phytomedicine* 2:363–386 (Mar. 1996).

Massiot, G., and Lavaud, C., "Structural Elucidation of Saponins," *Studies in Natural Products Chemisrty* 15:187–224 (1995).

Newman, M.J., et al., "Saponin Adjuvant Induction of Ovalbumin–Specific $CD8^+$ Cytotoxic T Lymphocyte Responses," *J. Immunol.* 148:2357–2362 (1992).

Osbourn, A.E., et al., "Saponin Detoxification by Plant Pathogenic Fungi," *Saponins Used in Traditional and Modern Medicine,* Waller, G.R., and Yamasaki, K., Eds., Plenum Press: New York, N.Y., pp. 547–555 (1996).

Pillion, D.J., et al., "DS–1, a Modified *Quillaja Saponin,* Enhances Ocular and Nasal Absorption of Insulin," *J. Pharm. Sci.* 84:1276–1279 (1995).

Pillion, D.J., et al., "Structure–function Relationship among *Quillaja Saponins* Serving as Excipients for Nasal and Ocular Delivery of Insulin," *J. Pharm. Sci.* 85:518–524 (1996).

Price, K.R., et al., "The Chemistry and Biological Significance of Saponins in Foods and Feedingstuffs," *CRC Crit. Rev. Food Sci. Nutr.* 26:27–135 (1987).

Recchia, J., et al., "A Semisynthetic *Quillaja Saponin* as a Drug Delivery Agent for Aminoglycoside Antibiotics," *Pharm. Res.* 12:1917–1923 (1995).

Reid, G., "Soluble proteins incorporate into ISCOMs after covalent attachment of fatty acid," *Vaccine* 10:597–602 (1992).

Schöke, Th., and Hiller, K., "Triterpenoid saponins. Part 6," *Pharmazie* 5:313–342 (1990).

Scott, M.T., et al., "Adjuvant Activity of Saponin: Antigen Localization Studies," *Int. Arch. Allergy Appl. Immun.* 77:409–412 (1985).

Sela, M., "Antigenicity: Some Molecular Aspects," *Science* 166:1365–1374 (1969).

Shibata, S., "Saponins with Biological and Pharmacological Activity," New Natural Products and Plant Drugs with Pharmacological, Biological or Therapeutical Activity, Wagner, H., and Wolff, P., Eds., Springer–Verlag: Berlin, pp. 177–196 (1977).

International Search Report for International Application No. PCT/US98/10280, mailed Oct. 13, 1998.

Kensil, C.R., et al., "Structure/Function Studies on QS–21, a Unique Immunological Adjuvant from *Quillaja saponaria,*" *Saponins Used in Traditional and Modern Medicine,* Waller, G.R., and Yamasaki, K., eds., Plenum Press: New York, N.Y., pp. 165–172 (1996).

Kensil, C.R., et al., "Structure/Function Relationship in Adjuvants from *Quillaja saponaria* Molina," *Vaccines* 92:35–40 (1992).

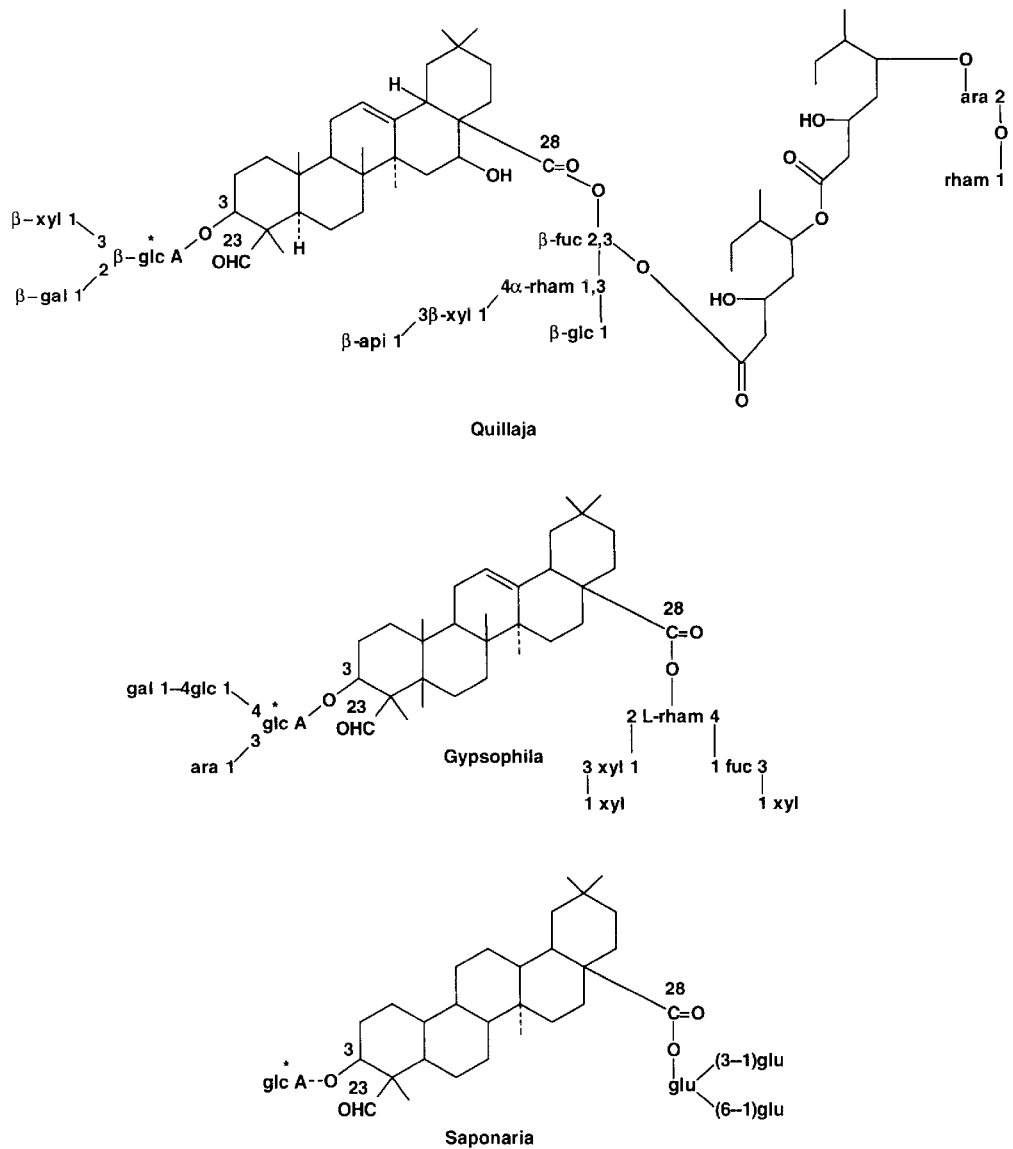
FIG 1. Saponin Adjuvants

Quillaja

IMMUNOSTIMULATING AND VACCINE COMPOSITIONS EMPLOYING SAPONIN ANALOG ADJUVANTS AND USES THEREOF

CROSS-REFERENCE TO RELATED APPLICATIONS

This application is a continuation-in-part of appliaction Ser. No. 09/081,647, filed May 20, 1998, now allowed as U.S. Pat. No. 5,977,081 which application claims the benefit under 35 U.S.C. § 119(e) of U.S. provisional applications No. 60/047,129, filed May 20, 1997 and No. 60/080,389, filed Apr. 2, 1998, both of which are entirely incorporated by reference herein.

BACKGROUND OF THE INVENTION

1. Field of the Invention

The present invention is in the field of adjuvants and immunostimulating agents. More particularly, the invention pertains to vaccines and immunostimulating compositions that include saponin-lipophile conjugate adjuvants.

2. Related Art

Saponins are glycosidic compounds that are produced as secondary metabolites. They are widely distributed among higher plants and in some marine invertebrates of the phylum Echinodermata (ApSimon et al., *Stud. Org. Chem.* 17:273–286 (1984)). Because of their antimicrobial activity, plant saponins are effective chemical defenses against microorganisms, particularly fungi (Price et al., *CRC Crit. Rev. Food Sci. Nutr.* 26:27–135 (1987)). Saponins are responsible for the toxic properties of many marine invertebrates (ApSimon et al., *Stud. Org. Chem.* 17:273–286 (1984)). The chemical structure of saponins imparts a wide range of pharmacological and biological activities, including some potent and efficacious immunological activity. In addition, members of this family of compounds have foaming properties (an identifying characteristic), surfactant properties (which are responsible for their hemolytic activity), cholesterol-binding, fungitoxic, molluscicidal, contraceptive, growth-retarding, expectorant, antiinflammatory, analgesic, antiviral, cardiovascular, enzyme-inhibitory, and antitumor activities (Hostettmann, K., et al., *Methods Plant Biochem.* 7:435–471(1991); Lacaille-Dubois, M. A. & Wagner, H., *Phytomedicine* 2:363–386 (1996); Price, K. R., et al., *CRC Crit. Rev. Food Sci. Nutr.* 26:27–135 (1987)).

Structurally, saponins consist of any aglycone (sapogenin) attached to one or more sugar chains. In some cases saponins may be acylated with organic acids such as acetic, malonic, angelic and others (Massiot, G. & Lavaud, C., *Stud. Nat. Prod. Chem.* 15:187–224(1995)) as part of their structure. These complex structures have molecular weights ranging from 600 to more than 2,000 daltons. The asymmetric distribution of their hydrophobic (aglycone) and hydrophilic (sugar) moieties confers an amphipathic character to these compounds which is largely responsible for their detergent-like properties. Consequently, saponins can interact with the cholesterol component of animal cell membranes to form pores that may lead to membrane destruction and cell death, such as the hemolysis of blood cells.

Triterpene Glycoside

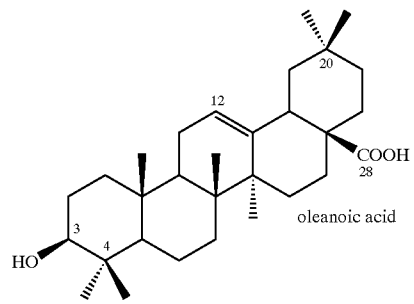

oleanoic acid

Steroid Glycoside

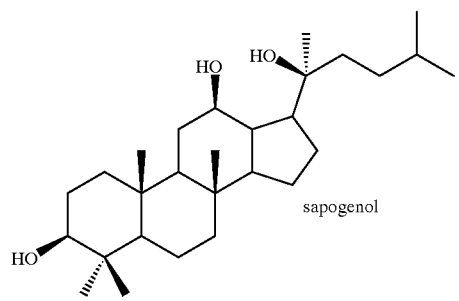

sapogenol

Alkaloid Glycoside

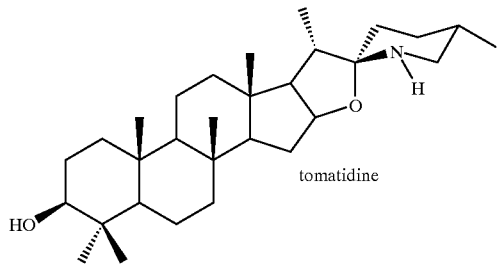

tomatidine

Saponins can be classified according to their aglycone composition as shown above:
1. Triterpene glycosides
2. Steroid glycosides
3. Steroid alkaloid glycosides The steroid alkaloid glycosides, or glycoalkaloids, share many physical and biological properties with steroid glycosides, but alkaloid glycosides are usually considered separately because their steroidal structure contains nitrogen. Frequently, the aglycones have methyl substituents that may be oxidized to hydroxymethyl, aldehyde or carboxyl groups; these moieties may play a role in some of the saponin's biological activities. From extensive studies of saponins, it is apparent that the triterpene saponins are not only the most predominant in nature, but also those with the most interesting biological and pharmacological properties.

Saponins have one or more linear or branched sugar chains attached to the aglycone via a glycosidic ether or ester link. In some saponins, the presence of acylated sugars has also been detected. According to the number of sugar chains attached to the aglycone, the saponins can be monodesmosidic saponins (with a single sugar chain), or bidesmosidic saponins (with two sugar chains). In the monodesmosidic saponins, the sugar chain is typically attached by a glycosidic ether linkage at the C-3 of the aglycone. In addition to the C-3 linked sugar chain, bidesmosidic saponins have a second sugar chain bound at C-28 (triterpene saponins) or at C-26 (steroid saponins) by an ester linkage. Because of the typical lability of esters, bidesmosidic saponins are readily converted into their monodesmosidic forms by mild hydrolysis (Hostettmann, K., et al., *Methods Plant Biochem.* 7:435–471 (1991)) (FIG. 2). Apparently, monodesmosidic saponins are significantly more biologically active in plants than their bidesmosidic forms. For instance, in Hedera helix the enzymatic transformation of the bidesmosidic hederasaponin C to its monodesmosidic form (α-hederin) results in a product with a high antibiotic activity (Wagner, H. & Horhammer, L., *Pharmacognosy and Phytochemistry*, Springer-Verlag, Berlin (1971)). In general, monodesmosidic saponins also tend to be more hemolytic than bidesmosidic saponins. This property appears to correlate well with their antifungal activity. Presumably, by interacting with the fungi's membrane-bound sterols, saponins alter the permeability of cell membranes leading to the organism's death (Price, K. R., et al., *CRC Crit. Rev. Food Sci. Nutr.* 26:27–135 (1987)). Consequently, the host range of plant pathogenic fungi appears to be functionally determined by their capacity to enzymatically detoxify the host organism's saponins (Bowyer, P., et al., *Science* 267: 371–374 (1995)). However, the acylated quillaja saponins appear to be exceptional since their monodesmosidic forms are significantly less effective hemolytic agents than their acylated and non-acylated bidesmosidic forms (Pillion, D. J., et al., *J. Pharm. Sci.*, 84:1276–1279 (1996)). Bidesmosidic saponins most likely function as useful forms for storage and/or transport of these compounds until such time as the biologically active monodesmosidic forms are required for the plant's defense (Hostettmann, K., et al., *Methods Plant Biochem.* 7:435–471 (1991); Osbourn, A. E., et al.,*Adv. Exp. Med. Biol.*, 404:547–555 (1996)). In contrast, in animals, bidesmosidic saponins may have potent biological and pharmacological activities that are completely unrelated to any aspects of plant physiology.

Saponin adjuvants from the bark of the *Quillaja saponaria* Molina tree (Quillajasaponins) are chemically and immunologically well-characterized products (Dalsgaard, K. *Arch. Gesamte Virusforsch.* 44:243 (1974); Dalsgaard, K., *Acta Vet. Scand.* 19 (Suppl. 69):1 (1978); Higuchi, R. et al., *Phytochemistry* 26:229 (1987); ibid. 26:2357 (1987); ibid. 27:1168 (1988); Kensil, C. et al., *J. Immunol.* 146:431 (1991); Kensil et al., U.S. Pat. No. 5,057,540 (1991); Kensil et al., *Vaccines* 92:35 (1992); Bomford, R. et al., *Vaccine* 10:572 (1992); and Kensil, C. et al., U.S. Pat. No. 5,273,965 (1993)).

These saponin adjuvants are a family of closely related O-acylated triterpene glycoside structures. They have an aglycone triterpene (quillaic acid), with branched sugar chains attached to positions 3 and 23, and an aldehyde group in position 23. A unique characteristic of the Quillajasaponins is the presence of acyloil acyl moieties linked at the C-3 hydroxy group of a fucopyranose bound by an ester bond to position 28 of quillaic acid. These acyl moieties have been identified as 3,5-dihydroxy-6-methyloctanoic acid, 3,5-dihydroxy-6-methyloctanoic acid 5-O-α-L-rhamnopyranosyl-(1→2)-α-L-arabinofuranoside, and 5-O-α-L-arabinofuranoside.

Higuchi, R. et al. (*Phytochemistry* 26:229 (1987); ibid. 27:1168 (1988), and Kensil, C. et al. (U.S. Pat. No. 5,057,540, ibid., *Vaccine* 92:35 (1992), and U.S. Pat. No. 5,273,965 (1993)) have demonstrated that the 3-O-glycosidic linkage between the fucosyl residue and the acyloyl acyl residue can be cleaved by mild alkaline hydrolysis to yield desacylsaponins. These desacylsaponins from Quillajasaponins are more hydrophilic than the original saponins. Apparently, deacylation of Quillajasaponins results in a significant loss of adjuvant activity, as measured by antibody production and CTI response (Kensil et al., U.S. Pat. No. 5,057,540 at column 22, lines 35 to 49; Kensil et al., *Vaccines* 92:35 (1992); and Kensil et al., U.S. Pat. No. 5,273,965, column 7, line 62).

Quillajasaponins are found as a mixture of about twenty structurally closely related triterpenoid glycosides with minimal differences between them (Higuchi, R. et al., *Phytochemistry* 26:229 (1987); ibid., 26:2357 (1987); ibid., 27:1169 (1988); Kensil et al., U.S. Pat. No. 5,057,540 (1991); Kensil et al., *Vaccines* 92:35 (1992)), making their separation difficult. Their triterpenoid group carries the aldehyde group responsible for inducing T-cell immunity, whereas their carbohydrate moieties seem to enhance humoral immunity (perhaps by interacting with lymphocyte receptors) in a fashion similar to certain polysaccharides (Bohn J. and J. BeMiller, *Carbohydrate Polymers* 28:3 (1995). In effect, PCT published application WO 90/03184 describes that saponins with their triterpenoid aldehyde reduced to alcohol are still able to induce an antibody response. Another component of quillajasaponins, the acyloyl-acyl groups, likewise appear to play a role in adjuvanticity. There are also reasons to suspect that their acyloyl acyl moiety, formed by a normoterpene carboxylic acid, is in part responsible for some of the toxic properties observed with several of the purified Quillajasaponins (Kensil, C. et al., *J. Immunol.* 146:431 (1991)). Thus, it would be of commercial interest to develop modified Quillajasaponins which are easier to purify, potentially less toxic, chemically more stable, and with equal or better adjuvant properties than the original saponins.

The immune system may exhibit both specific and non-specific immunity (Klein, J., et al., *Immunology* (2nd), Blackwell Science Inc., Boston (1997)). Generally, B and T lymphocytes, which display specific receptors on their cell surface for a given antigen, produce specific immunity. The immune system may respond to different antigens in two ways: 1) humoral-mediated immunity, which includes B cell stimulation and production of antibodies or immunoglobulins [other cells are also involved in the generation of an antibody response, e.g. antigen-presenting cells (APCs; including macrophages), and helper T cells (Th1 and Th2)], and 2) cell-mediated immunity (CMI), which generally involves T cells including cytotoxic T lymphocytes (CTLs), although other cells are also involved in the generation of a CTL response (e.g., Th1 and/or Th2 cells and APCs).

Nonspecific immunity encompasses various cells and mechanisms such as phagocytosis (the engulfing of foreign particles or antigens) by macrophages or granulocytes, and natural killer (NK) cell activity, among others. Nonspecific immunity relies on mechanisms less evolutionarily advanced (e.g., phagocytosis, which is an important host defense mechanism) and does not display the acquired nature of specificity and memory, hallmarks of a specific immune response. Nonspecific immunity is more innate to vertebrate systems. In addition, cells involved in nonspecific immunity interact in important ways with B and T cells to produce an immune response. The key differences between specific and nonspecific immunity are based upon B and T cell specificity. These cells predominantly acquire their responsiveness after activation with a specific antigen and have mechanisms to display memory in the event of future exposure to that specific antigen. As a result, vaccination (involving specificity and memory) is an effective protocol to protect against harmful pathogens.

A critical component of inactivated vaccines, including subunit vaccines, is an adjuvant. Immune adjuvants are compounds that, when administered to an individual, increase the immune response to an antigen in a test subject to which the antigen is administered, or enhance certain activities of cells from the immune system. Some antigens are weakly immunogenic when administered alone or are toxic to a subject at concentrations that evoke useful immune responses in a subject. In these cases, an immune adjuvant can be used to enhance the immune response of the subject to the antigen by making the antigen more strongly immunogenic. The adjuvant may also allow the use of a lower dose of antigen to achieve a useful immune response in a subject.

Immune adjuvants can modify or immunomodulate the cytokine network, up-regulating the humoral and cellular immune response. Humoral response elicits antibody formation. Cellular immune response involves the activation of T cell response, Th1 or Th2, to mount this immune response. Th1 responses will elicit complement fixing antibodies and strong delayed-type hypersensitivity reactions associated with IL-2, IL-12, and γ-interferon. Induction of cytotoxic T lymphocytes (CTLs) response also appears to be associated with a Th1 response. Th2 responses are associated with high levels of IgE, and the cytokines IL-4, IL-5, IL-6, and IL-10. The aldehyde-containing saponins such as those from quillaja induce a strong Th1 response. However, some of their analogs may induce a Th2 response.

Adjuvants that have been used to enhance an immune response include aluminum compounds (all generally referred to as "alum"), oil-in-water emulsions (often containing other compounds), complete Freund's adjuvant (CFA, an oil-in-water emulsion containing dried, heat-killed Mycobacterium tuberculosis organisms), and pertussis adjuvant (a saline suspension of killed *Bordatella pertussis* organisms). These adjuvants generally are thought to have their mechanism of action by causing a depot of antigen and permitting a slow release of the antigen to the immune system, and by producing nonspecific inflammation thought to be responsible for their observed activity (Cox, J. C., et al., *Vaccine* 15:248–256 (1997)). Some saponins have been shown to have different types of immune stimulating activities, including adjuvant activity. These activities have been reviewed previously (Shibata, S., *New Nat. Prod. Plant Pharmacol. Biol. Ther. Act., Proc. Int. Congr.* 1st, 177–198 (1977); Price, K. R., et al. *CRC Crit. Rev. Food Sci. Nutr.* 26:27–135 (1987); Schöpke, Th., & Hiller, K., *Pharmazie* 45:313–342 (1990); Lacaille-Dubois, M. A., et al., *Phytomedicine* 2:363–386 (1996)).

PCT published application WO 93/05789 describes conjugates in which poorly immunogenic proteins are covalently attached to purified, acylated Quillaja saponin fraction via the carboxyl group of 3-O-glucuronic acid. Addition of free quillajasaponins to these conjugates induced a higher immune response suggesting (i) that the covalently attached quillajasaponin serves as an association site for additional saponin molecules and (ii) that the adjuvant effect depends on the number of saponins associated with the protein antigen.

PCT published application WO 90/03184 describes an immunostimulating complex (ISCOM) comprising at least one lipid and at least one saponin, and that may optionally include adjuvants in addition to the saponin. These matrices are taught to be useful as immunomodulating agents and vaccines. The lipid and saponin are in a physical association, rather than covalently attached to one another. Quil A (a Quillaja saponin extract) is the preferred saponin. The reference additionally teaches that it is beneficial to add adjuvants (in addition to Quil A) to the ISCOM matrix. The reference teaches that an adjuvant lacking suitable hydrophobic properties may be modified to comprise a hydrophobic domain for incorporation into the ISCOM matrix.

Bomford, R. et al., *Vaccine* 10:572–577 (1992) teaches that lipids can be mixed with a variety of saponins to form ISCOM'S. The reference teaches that Quillaja saponins, Gypsophila saponins and Saponaria saponins were the only saponins tested that were adjuvant active.

There remains a need for adjuvants that have enhanced adjuvanticity and lower toxicity.

SUMMARY OF THE INVENTION

The present invention is directed to vaccine compositions comprising:
(a) one or more bacterial, viral or tumor—associated antigens, and
(b) a saponin-lipophile conjugate, in which
 (1) a non-acylated or deacylated triterpene saponin having a 3-O-glucuronic acid residue is covalently attached, either directly or via a linking moiety, to:
 (2) a compound having a lipophilic domain, such as a fatty acid, fatty amine, phospholipid, terpene, polyethylene glycol, among others;
 wherein (1) is attached to (2) via the carboxyl carbon atom present on the 3-O-glucuronic acid residue of the triterpene saponin.

Useful antigens are peptide, polypeptide, oligosaccharide or ganglioside antigens associated with a pathogen such as a bacterium or virus that causes illness in a human or animal; or antigens associated with the presence of cancer in a human or animal.

The present invention is also directed to a method of vaccination, comprising administering a vaccine composition of the present invention.

The present invention is also directed to a method of potentiating an immune response to an antigen, comprising administering a vaccine of the present invention to an animal in need thereof.

The present invention is also directed to pharmaceutical and veterinary compositions comprising one or more of the saponin-lipophile conjugates, and one or more pharmaceutically acceptable diluents, carriers or excipients. These compositions may be employed as immunopotentiators in animals and humans.

DETAILED DESCRIPTION OF THE PREFERRED EMBODIMENTS

Figure 1A:
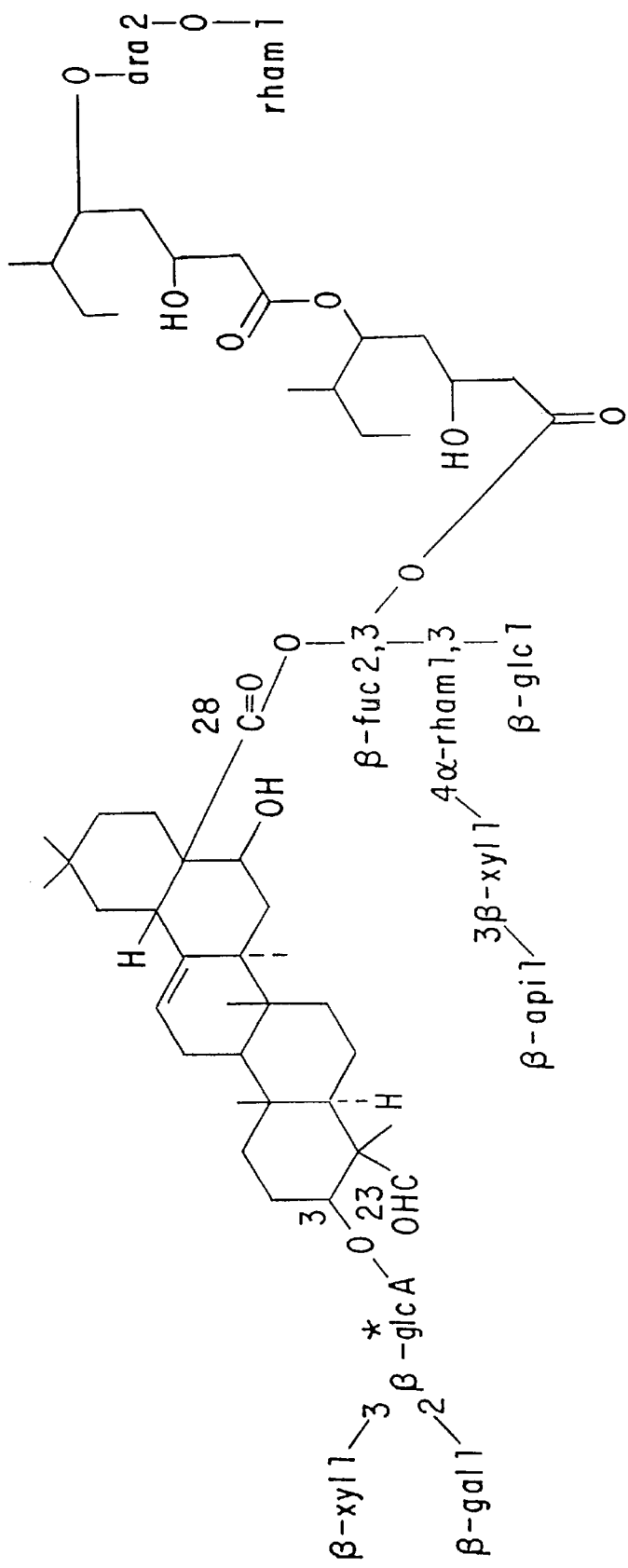
FIG. 1 illustrates representative chemical structures for saponins that are derived from Quillaja, Gypsophila and Saponaria.

The present invention is directed to pharmaceutical and veterinary compositions that comprise:
(a) one or more bacterial, viral, protozoal or tumor-associated antigens; and
(b) a saponin-lipophile conjugates, in which
(1) a non-acylated or deacylated triterpene saponin having a 3-O-glucuronic acid residue, is covalently attached to:
(2) a lipophilic moiety, for example, one or more fatty acids, fatty amines, aliphatic amines, aliphatic alcohols, aliphatic mercaptans, terpene or polyethylene glycols;
wherein (2) is attached to (1) via the carboxyl carbon atom present on the 3-O-glucuronic acid residue of the triterpene saponin, either directly or through an appropriate linking group.

In its broadest embodiment, the present invention relates to vaccines employing one or more modified saponin adjuvants wherein said modified saponins (a) have a triterpene aglycone core structure (such as quillaic acid, gypsogenin and others) with branched sugar chains attached to positions 3 and 28, and an aldehyde group linked or attached to position 4; (b) are either originally non-acylated, or require removal of an acyl or acyloyl group that is bound to a saccharide at the 28-position of the triterpene aglycone; and (c) have a lipophilic moiety covalently attached, either directly or through a linker moiety, to the carboxylic acid of glucuronic acid at the 3-position of the triterpene aglycone. These adjuvants are referred to herein as saponin-lipophile conjugates.

The phrases "lipophilic moiety" and "a residue of a lipophilic molecule," as used herein, refer to a moiety that is attached by covalent interaction of a suitable functional group of one or more compounds that are non-polar or have a non-polar domain with the 3-O-glcA residue of a saponin. The lipophilic moiety can be a portion of an amphipathic compound. An amphipathic compound is a compound whose molecules contain both polar and non-polar domains. Surfactants are examples of amphipathic compounds. Surfactants typically possess a non-polar portion that is often an alkyl, aryl or terpene structure. In addition, a surfactant possesses a polar portion, that can be anionic, cationic, amphoteric or non-ionic. Examples of anionic groups are carboxylate, phosphate, sulfonate and sulfate. Examples of cationic domains are amine salts and quaternary ammonium salts. Amphoteric surfactants possess both an anionic and cationic domain. Non-ionic domains are typically derivatives of a fatty acid carboxy group and include saccharide and polyoxyethylene derivatives.

A lipophilic moiety can also comprise two or more compounds possessing non-polar domains, wherein each of the compounds has been completely bonded to a linking group, which, in turn, is covalently attached to the 3-O-glucoronic acid.

Several lipophile-containing compounds, such as aliphatic amines and alcohols, fatty acids, polyethylene glycols terpenes and amphipathic molecules, can be added to the 3-O-glcA residue of deacylsaponins and to the 3-O-glcA residue of non-acylated saponins. The lipophile may be an aliphatic or cyclic structure that can be saturated or unsaturated. By way of example, fatty acids, terpenoids, aliphatic amines, aliphatic alcohols, aliphatic mercaptans, glycosyl-fatty acids, glycolipids, phospholipids and mono- and di-acylglycerols can be covalently attached to non-acylated saponins or desacylsaponins. Attachment can be via a functional group on a lipophilic moiety that covalently reacts with either the acid moiety of the 3-glucuronic acid moiety, or an activated acid functionality at this position. Alternatively, a bifunctional linker can be employed to conjugate the lipophile to the 3-O-glcA residue of the saponin.

The desacylsaponins and non-acyl saponins may be directly linked to the lipophilic moiety or may be linked via a linking group. By the term "linking group" is intended one or more bifunctional molecules that can be used to covalently couple the desacylsaponins, non-acylated saponins or mixtures thereof to the lipophilic molecule. The linker group covalently attaches to the carboxylic acid group of the 3-O-glucuronic acid moiety on the triterpene core structure, and to a suitable functional group present on the lipophilic molecule. Useful linker groups include —NH—CH$_2$—CH$_2$—NH—, —NH—CH(COOH)—CH$_2$—NH—, —NH—CH$_2$—CH(COOH)—NH—, —NH—CH$_2$—CH$_2$—CH$_2$—NH—, —O—(CH$_2$)$_r$—NH—, —S—(CH$_2$)$_r$—NH—, —S—(CH$_2$)$_r$—C(O)—, —NH—CH$_2$—C(O)—, —O—CH$_2$—CH$_2$—O—CH$_2$—CH$_2$—O—, —NH—NH—C(O)—CH$_2$—, —NH—C(CH$_3$)$_2$—C(O)—, and —NH—NH—C(O)—(CH$_2$)$_r$—C(O)—NH—N=, where r, in each instance, is from 2–5.

Non-limiting examples of linker groups which can be used to link the saponin and lipophilic molecule are alkylene diamines (NH$_2$—(CH$_2$)$_n$—NH$_2$), where n is from 2 to 12; aminoalcohols (HO—(CH$_2$)$_r$—NH$_2$), where r is from 2 to 12; and amino acids that are optionally carboxy-protected; ethylene and polyethylene glycols (H—(O—CH$_2$—CH$_2$)$_n$—OH, where n is 1–4) aminomercaptans and mercaptocarboxylic acids.

Antigens from a variety of pathogenic agents can be employed in combination with the saponin lipophile adjuvants to form the vaccine formulations of the present invention.

As used herein, the phrase "pathogenic agent" means an agent which causes a disease state or affliction in an animal. Included within this definition, for examples, are bacteria, protozoans, fungi, viruses and metazoan parasites which either produce a disease state or render an animal infected with such an organism susceptible to a disease state (e.g., a secondary infection).

As used herein, the term "organism" means any living biological system, including viruses, regardless of whether it is a pathogenic agent.

As used herein, the term "antigen" means a substance that has the ability to induce a specific immune response. For purposes of the present invention, the term "antigen" is used interchangeably with immunogen.

An "immunogenic epitope" is defined as a part of a protein that elicits an antibody response when the whole protein or polypeptide is the immunogen. These immunogenic epitopes are believed to be confined to a few loci on the molecule. On the other hand, a region of a protein molecule to which an antibody can bind is defined as an "antigenic determinant" or "antigenic epitope." The number of immunogenic epitopes of a protein generally is less than the number of antigenic epitopes. See, for instance, Geysen et al., Proc. Natl. Acad. Sci. USA 81:3998–4002 (1983).

Additional definitions are provided throughout the specification.

Vaccines of the present invention can include one or more bacterial antigens from a particular bacteria. Bacteria for which vaccines can be formulated include: *Helicobacter pylori, Chlamydia pneumoniae, Chlamydia trachomatis, Ureaplasma urealyticum, Mycoplasma pneumoniae,* Staphylococcus spp., *Staphylococcus aureus,* Streptococcus spp., *Streptococcus pyogenes, Streptococcus pneumoniae, Streptococcus viridans, Enterococcus faecalis, Neisseria meningitidis, Neisseria gonorrhoeae, Bacillus anthracis,* Salmonella spp., *Salmonella typhi, Vibrio cholera, Pasteurella pestis, Pseudomonas aeruginosa,* Campylobacter spp., *Campylobacter jejuni,* Clostridium spp., *Clostridium difficile,* Mycobacterium spp., *Mycobacterium tuberculosis,* Treponema spp., Borrelia spp., *Borrelia burgdorferi,* Leptospira spp., *Hemophilus ducreyi, Corynebacterium diphtheria, Bordetella pertussis, Bordetella parapertussis, Bordetella bronchiseptica, hemophilus influenza, Escherichia coli,* Shigella spp., Erlichia spp., and Rickettsia spp.

Bacterial antigens can be native, recombinant or synthetic. Such bacterial antigens include, but are not limited to, selectins or lectins from bacteria that bind to carbohydrate determinants present on cell surfaces; and bacteria receptors for proteins, such as fibronectin, laminin, and collagens.

Vaccines of the present invention can include one or more one or more antigens from a particular virus to form a vaccine. Viruses for which vaccines can be formulated include: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease virus.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses. Additionally, peptides derived from such viral proteins can be employed, can be employed, either free, or associated non-covalently, or conjugated covalently to a suitable carrier.

Vaccines of the present invention can include one or more tumor associated antigens. Tumor associated antigens can be native, recombinant or synthetic. Such tumor associated antigens include, but are not limited to, killed tumor cells and lysates thereof, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210^{BCR-ABL}$.

Peptides that are derived from these tumor associated antigens can be employed, either free, or non-covalently associated, or conjugated covalently to a suitable carrier. Alternatively, gangliosides can be employed, either free, non-covalently associated or conjugated covalently to a suitable carrier; or oligosaccharide sequences that are specific or predominantly found in cancer cells can be employed either free, non-covalently associated or conjugated covalently to a suitable carrier.

The attachment of a lipophilic moiety to the 3-O-glucuronic acid of a saponin, such as Quillaja desacylsaponins, *Silene jenisseenis* Willd's desacylsaponins, lucyoside P, and Gypsophila Saponaria and *Acanthophyllum squarrosum's* saponins enhances their adjuvant effects on humoral and cell mediated immunity. Additionally, the attachment of a lipophilic moiety to the 3-O-glucuronic acid residue of nonacylated or deacylated saponin yields a saponin analog that is easier to purify, less toxic, chemically more stable, and possesses equal or better adjuvant properties than the original saponin.

Useful fatty acids include $C_6$–$C_{24}$ fatty acids, preferably $C_7$–$C_{18}$ fatty acids. Examples of useful fatty acids include saturated fatty acids such as lauric, myristic, palmitic, stearic, arachidic, behenic, and lignoceric acids; and unsaturated fatty acids, such as palmitoleic, oleic, linoleic, linolenic and arachidonic acids.

Useful aliphatic amines, aliphatic alcohols and aliphatic mercaptans include amines and alcohols and mercaptans (RSH) having a straight-chained or branched, saturated or unsaturated aliphatic group having about 6 to about 24 carbon atoms, preferably 6 to 20 carbon atoms, more preferably 6 to 16 carbon atoms, and most preferably 8 to 12 carbon atoms. Examples of useful aliphatic amines include octylamine, nonylamine, decylamine, dodecylamine, hexadecylamine, sphingosine and phytosphingosine. Examples of useful aliphatic alcohols include octanol, nonanol, decanol, dodecanol, hexadecanol, chimyl alcohol and selachyl alcohol.

Useful terpenoids include retinol, retinal, bisabolol, citral, citronellal, citronellol and linalool.

Useful mono- and di-acylglycerols include mono-, and di-esterified glycerols, wherein the acyl groups include 8 to 20 carbon atoms, preferably 8 to 16 carbon atoms.

Useful polyethylene glycols have the formula H—(O—$CH_2$—$CH_2$)$_n$OH, where n, the number of ethylene oxide units, is from 4 to 14. Examples of useful polyethylene glycols include PEG 200 (n=4), PEG 400 (n=8–9), and PEG 600 (n=12–14).

Useful polyethylene glycol fatty alcohol ethers, wherein the ethylene oxide units (n) are between 1 to 8, and the alkyl group is from $C_6$ to $C_{18}$.

A side-chain with amphipathic characteristics, i.e. asymmetric distribution of hydrophilic and hydrophobic groups, facilitates (a) the formation of micelles as well as an association with antigens, and (b) the accessibility of the triterpene aldehyde to cellular receptors. It is also possible that the presence of a negatively-charged carboxyl group in such a side-chain may contribute to the repulsion of the triterpene groups, thus allowing them a greater degree of rotational freedom. This last factor would increase the accessibility of cellular receptors to the imine-forming carbonyl group.

The present invention is useful with any saponin meeting the above-described structural requirements for the reasons described herein.

The term "non-acylated saponin" or "non-acyl saponin," as employed herein, refers to a saponin that lacks an acyl or acyloyl group attached to an oligosaccharide residue which itself is attached to the 28-position of the triterpene.

The term "deacylsaponin" or "deacylated saponin," as employed herein, refers to a saponin that has been modified to remove an acyl or acyloyl group from an oligosaccharide residue which itself is attached to the 28-position of the triterpene.

Quillaja, Gypsophila and Saponaria are useful saponins, all having triterpene aglycones with an aldehyde group linked or attached to position 4, branched oligosaccharides linked by an ester bond in position 28, and a 3-O-glucuronic acid (3-O-glcA) that in Quillaja and Gypsophila is linked to branched oligosaccharides. Saponins from *Q. saponaria* and *S. jenisseenis* include acyl moieties, whereas saponin from Gypsophila, Saponaria, and Acanthophyllum do not include acyl moieties. Each of these non-acylated or de-acylated saponins is useful in the present invention.

Other triterpene saponin are also suitable for preparation of the lipid conjugates that are the subject of this application. These new saponin have structural characteristics similar to those saponins from *Quillaja saponaria* Molina, Gypsophila sp., or *Saponaria officinalis*; i.e., they have an aldehyde and a gluconuric acid residue linked to their aglycones. These additional saponins are the bidesmosidic saponin, squarroside A, isolated from *Acanthophyllum squarrosum*; the saponin lucyoside P; and two acylated saponins isolated from *Silene jenisseensis* Willd. Following is a brief description of these compounds.

Squarroside A is abidesmosidic saponin that contains two oligosaccharide chains linked to C-3 and C-28 of its aglycone gypsogenin. Similar to the gypsophila saponin, it has an aldehyde group linked to C-4 of the aglycone, and a glucuronic acid residue at C-3. In addition, it contains an acetylated fucose residue at C-28. It has been shown that squarroside A has immunomodulating activity as measured by an in vitro lymphoproliferative test. These apparently nonspecific immunomodulating effects were dose-dependent: a suppressive effect at concentrations in the $\mu$g range and a stimulant effect in the pg range.

Lucyoside P is a bidesmosidic saponin that has carbohydrate residue linked to C-3 and C-28 of its aglycone quillaic acid, and an aldehyde group at C-4. Lucyoside P has a glucuronic acid residue at C-3.

Two acylated saponins have been isolated from the Caryophyllacea *Silene jenisseensis*. These saponins have carbohydrates linked to C-3 and C-28 of their agylcone quillaic acid. The carbohydrate residues linked to C-3 and C-28 are glucuronic acid and fucose, respectively. The fucose residue is acylated with a p-methoxycinnamoyl group to yield trans- and cis-p-methoxycinnamoyl tritepene glycosides. Although these saponins have an aldehyde group, they have no apparent immunostimulating activity as detected by an in vitro chemiluminescence granulocyte assay. However, it is possible that the p-methoxycinnamoyl moiety is interfering with the activity of the reactive oxygen needed to produce chemiluminescence.

All of the previously described saponins have been isolated to purity. However, the acylated saponins from *Silene jenisseensis* have been obtained only as a mixture of the cis- and trans-isomeric forms. Similar to the *Q. saponaria* saponin, these acylated saponins from *Silene jenisseensis* are readily deacylated by a mild alkaline hydrolysis with ~0.2 N KOH for 1 hour at room temperature. The deacylated saponin is then modified by one of the procedures described herein to yield analogs with immunostimulatory and adjuvant activities.

In a preferred embodiment of the present invention, the saponin-lipophile conjugate is a desacylated quillajasaponin that has been conjugated to a lipophilic moiety via chemical reaction with the carboxylic group of the 3-O-glucuronic acid.

Thus, in this preferred embodiment of the present invention, vaccine compositions include a compound of Formula II:

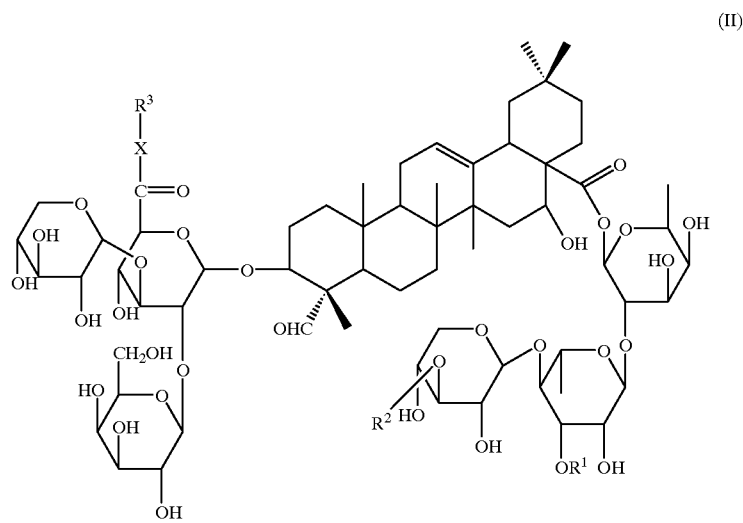

(II)

or a pharmaceutically acceptable salt thereof; wherein
$R^1$ is glucose or hydrogen; $R^2$ is apiose or xylose, preferably apiose; X is S, O, NH, —$NR^4$ or a linking group; $R^3$ and $R^4$ are each lower alkyl or a residue of a lipophilic molecule.

Preferred values of X include O and NH. In addition, a number of bifunctional linking groups are preferred. Useful examples include —NH—$CH_2$—$CH_2$—NH—, —NH—CH(COOH)—$CH_2$—NH—, —NH—$CH_2$—CH(COOH)—NH—, —NH—$CH_2$—$CH_2$—$CH_2$—NH—, —O—$(CH_2)_r$—NH—, —S—$(CH_2)_r$—NH—, —S—$(CH_2)_r$—C(O)—, —NH—$CH_2$—C(O)—, —O—$CH_2$—$CH_2$—O—$CH_2$—$CH_2$—O—, —NH—NH—C(O)—$CH_2$—, —NH—$C(CH_3)_2$—C(O)—, and —NH—NH—C(O)—$(CH_2)_r$—C(O)—NH—N=, where r, in each instance, is from 2–5.

Preferred $R^3$ groups include the residues of fatty acids, terpenoids, aliphatic amines, aliphatic alcohols, aliphatic mercaptans, polyethylene glycols, glycosyl-fatty acids, mono- and poly-$C_2$–$C_4$ alkyleneoxy derivatives of fatty acids and fatty alcohols, glycolipids, phospholipids and mono-, di- and tri-acylglycerols that are capable of being covalently attached to the 3-O-glcA carbonyl group or to a suitable functional group on a bifunctional linker.

Useful examples of $R^3$ residues include residues of arachidonic acid, caprylic acid, retinal, decanal, caprylaldehyde, nonylamine, nonanol, dodecylamine, dodecanol, octyl glucopyranoside, lauric acid, lauryl mercaptan, sphingosine, dihydrosphingosine, 4-octylbenzaldehyde, vitamin A, and glucosamine-ricinoleic acid conjugate.

In one aspect, $R^3$ is selected from the group consisting of a $C_4$–$C_{30}$ straight or branched chain alkyl group, and a $C_4$–$C_{30}$ straight or branched chain alkenyl group; either of which is optionally substituted by one or more of hydroxy, $C_1$–$C_6$ alkoxy, or mercapto, and is optionally interrupted by one or more components selected from the group consisting of NH, $N(R^{10})$, S, O, sulfinyl and sulfonyl groups, where $R^{10}$ is $C_{1-6}$ alkyl; and $R^4$ is $C_1$–$C_3$ alkyl, or is the same as $R^3$.

Non-limiting examples of adjuvants in this aspect of the present invention include compounds of Formula II where:

(a) $R^1$ is glucose; $R^2$ is apiose; X is NH; and $R^3$ is dodecyl;
(b) $R^1$ is glucose; $R^2$ is xylose; X is NH and $R^3$ is dodecyl;
(c) $R^1$ is hydrogen; $R^2$ is apiose; X is NH and $R^3$ is dodecyl;
(d) $R^1$ is hydrogen; $R^2$ is xylose; X is NH and $R^3$ is dodecyl;
(e) mixtures of (a)–(d);
(f) $R^1$ is glucose, $R^2$ is apiose; X is NH; and $R^3$ is nonyl;
(g) $R^1$ is glucose, $R^2$ is xylose; X is NH; and $R^3$ is nonyl;
(h) $R^1$ is hydrogen, $R^2$ is apiose; X is NH; and $R^3$ is nonyl;
(i) $R^1$ is hydrogen, $R^2$ is xylose; X is NH; and $R^3$ is nonyl; and
(j) mixtures of (f)–(i).

In another embodiment of the invention, the carboxylic acid moiety of the 3-glucuronic acid of Gypsophilia, Saponaria, Acanthophyllum saponin, the saponin lucyoside P, or deacylated saponin from S. jenisseenis is modified to provide conjugates where the acid has reacted with a suitable reagent to form an amide or ester linkage to a lipophilic moiety, either directly or via a suitable linker, as more fully described herein. The glucuronic acid is thereby converted to —C(O)—X—$R^3$, wherein X and $R^3$ are as defined above. Saponin-lipophile conjugates that are formed by reacting Gypsophilia and Saponaria saponins are represented by Formulae III and IV, respectively:

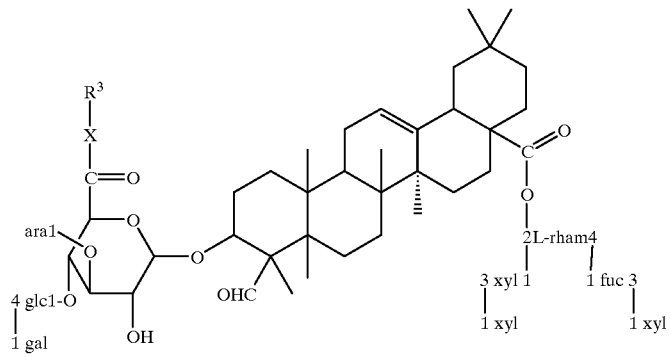

(III)

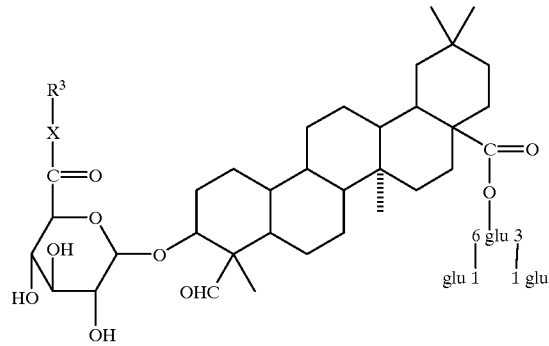

(IV)

wherein X and $R^3$ are as defined above.

An additional aspect of the present invention is directed to a saponin analog in which a biotinyl group has been added to the 3-O-glcA of a deacylated saponin or a non-acylated saponin, such as gypsophila and saponaria saponin. The incorporation of a biotinyl group allows for the binding of avidin or streptavidin that has been labeled with a detectable label such as a radioactive, fluorescent, paramagnetic or other type of tag or reporting group. Labeling of these compounds allows for their in vivo or in vitro detection for diagnostic purposes. For example, a FACS system can be employed for detection and determination of T-cells with cell-surface-receptors for the saponin analog. The presence of these receptors indicates which cells could potentially be stimulated by imine-forming groups to produce an immune response. Binding of the labeled avidin or streptavidin could take place either before or after the biotinylated saponin analog has bound to the cell-surface receptors.

Methods of Making

The saponin-lipophile conjugates that are employed in vaccines of the present invention, as well as useful starting materials, can be prepared according to the following procedures. Schemes to which reference is made are presented at the end of the description section, prior to the claims.

Preparation of Starting Materials

Mild alkaline hydrolysis of the Quillajasaponins mixture results in breakage of the 28-O-ester bond and deacylation of the saponins, yielding two main, closely related products differing in a single glucopyranosyl residue (Higuchi, R. et al., *Phytochemistry* 26:229 (1987); ibid., 26:2357 (1987); ibid., 27:1169 (1988); Kensil et al., U.S. Pat. No. 5,057,540 (1991); Kensil et al., *Vaccines* 92:35 (1992)). These two main desacylsaponins, which can be separated by chromatographic procedures, are more hydrophilic and have less adjuvanticity than the parent saponins. However, the reduction of over twenty Quillajasaponin species to just two compounds offers a practical source of starting materials for the development and production of semisynthetic adjuvants.

A preferred starting material is desacylated Quillajasaponins having Formula I:

where $R^1$ is glucose or hydrogen; and $R^2$ is apiose or xylose. In a preferred embodiment, by using the isolation procedures described herein, two desacylated Quillajasaponins, DS-1 and DS-2 can be isolated, and employed either singly or as a mixture. DS-1 refers to a compound of Formula I where $R^1$ is H; and $R^2$ is apiose or xylose. DS-2 refers to a compound of Formula I where $R^1$ is glucose; and $R^2$ is apiose or xylose.

Between 60%–70% of total desacylated quillajasaponins, representing DS-2 fraction, have a glucose residue at $R^1$. The other 30% to 40% of desacylated quillajasaponins (in which QS-21 derived product is the predominant), representing DS-1, do not have any glucose residues in their carbohydrate moiety. The extra glucose residue confers higher hydrophilicity to DS-2, which in reverse phase HPLC elutes earlier than DS-1. Most of the quillajasaponins have apiose at position $R^2$, except for a small portion of QS-21 which has xylose instead of apiose. The xylose substitute should be found mostly in the fraction DS-1. It is preferred to use the whole mixture of DS-1 and DS-2 to prepare conjugates.

There are two procedures which are based on mild alkaline hydrolysis to prepare the Quillaja desacylsaponins. The first procedure, described by Higuchi, R. et al. (*Phytochemistry* 26:229 (1987), fully incorporated by reference herein) starts with an alcoholic extract by Quillaja bark and the two desacylsaponins (1 and 2) are separated by chromatographic procedures (see Scheme 1). This method yields poor recoveries for both products.

A second procedure, described by Kensil, C. et al. (U.S. Pat. No. 5,057,540, fully incorporated by reference herein) starts with Quillajasaponins partially purified by ultrafiltration or by gel chromatography (Dalsgaard, *Arch. Gesamte Virusforsch.* 44:243 (1974); *Acta Vet. Scand.* 19 (*Suppl.* 69):1 (1978)). The desacylsaponins 1 (DS-1) and 2 (DS-2) are resolved by chromatographic methods. This procedure yields good recoveries for both products.

A further scheme for the preparation and isolation of desacylsaponins 1 and 2 is shown in Scheme 2. The desacylsaponins 1 and 2 are separated prior to their chemical modification. In some instances, depending on the toxicity, reproducibility, efficacy, and potential regulatory issues, it would be possible to use the modified mixture of 1 and 2 as an adjuvant.

(I)

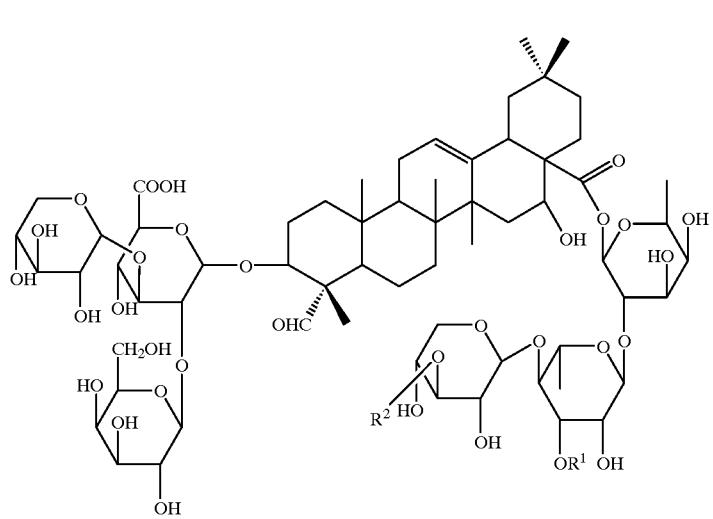

Deacylated saponin from a *S. jenisseensis* saponin can be formed by basic hydrolysis as well. See Scheme 3. The hydrolysis reaction results in removal of a trans-p-methoxycinnamoyl group.

Saponin-Lipophile Conjugates

Because the 3-O-glcA residue in Quillajasaponins can be modified without altering adjuvanticity, this carboxyl group offers a unique site for chemical modification of the desacylsaponins. Without wishing to be bound by theory, incorporation of a lipophilic or amphiphilic chain at the 3-O-glcA functionally substitutes for the 28-O-acyl group removed from Quillajasaponins by the alkaline hydrolysis. This modification yields neo-saponins with different physico-chemical properties and adjuvanticity comparable or better than that of the original Quillajasaponins. This modification can also be used with the non-acylated saponins from Gypsophila sp., *Saponaria officinalis* and the saponin squarroside and lucyoside P to improve their adjuvant effect on the primary immunoresponse.

The desacylsaponins and non-acylated saponins can be linked to the lipophilic or amphiphilic molecule by preparing an active ester of glucuronic acid, followed by reacting the active ester with a nucleophilic functional group on the linker or lipophilic molecule. Examples of the active esters which can be used in the practice of the invention include the glucuronate of N-hydroxysuccinimide, sulfo-N-hydroxysuccinimide, hydroxybenzotriazole, and p-nitrophenol. The active esters may be prepared by reacting of the carboxy group of the saponin with an alcohol in the presence of a dehydration agent such as dicyclohexylcarbodiimide (DCC), 1-(3-dimethylaminopropyl)-3-ethylcarbodiimide (EDC), and 1-(3-dimethylaminopropyl)-3-ethylcarbodiimide methiodide (EDCI). The linker or lipophilic/amphiphilic molecule is then mixed with the activated ester in aqueous solution to give the conjugate.

Where a linker group between the saponin and the lipophilic or amphiphilic molecule is desired, the active ester of the saponin glucuronate is prepared as described above and reacted with the linker group, e.g. 2-aminoethanol, an alkylene diamine, an amino acid such as glycine, or a carboxy-protected amino acid such as glycine tert-butyl ester. If the linker contains a protected carboxy group, the protecting group is removed and the active ester of the linker is prepared (as described above). The active ester is then reacted with the lipophilic molecule to give the conjugate. Alternatively, the lipophilic molecule may be derivatized with succinic anhydride to give a lipophile-succinate conjugate which may be condensed in the presence of EDC or EDCI with a saponin-linker derivative having a free amino or hydroxyl group on the linker.

It is also possible to prepare a saponin-linker conjugate comprising a linker with a free amino group (derived from an alkylene diamine) and crosslink the free amino group with a heterobifunctional cross-linker such as sulfosuccinimidyl 4-(N-maleimidocyclohexane)-1-carboxyl ate which will subsequently react with the free sulfhydryl groups of lipophilic thiol compound. Examples of such linkers include amino alcohols such as 2-aminoethanol and diamines such as ethylenediamine, 1,2-propylenediamine, 1,5-pentanediamine, 1,6-hexanediamine, and the like. The lipophilic molecule can then be coupled to the linker by first forming the succinated derivative with succinic anhydride followed by condensation with the saponin-linker conjugate with DCC, EDC or EDCI.

Fatty Acid-Desacylsaponin Conjugates

Fatty acids are suitable for modifying the 3-O-glcA residue of desacylsaponins. Certain unsaturated fatty acids, such as arachidonic acid, have a series of double bonds that impose a rigid structure similar to the terpenoids, and are preferred. Other examples of preferred fatty acids include caprylic acid, caproic acid, capric acid, linoleic acid, palmitic acid, ricinoleic acid, oleic acid, palmitoleic acid, pelargonic acid, lauric acid, and eicosapentanoic acid.

Using the carbodumide or the mixed anhydride procedures, a diamine can be coupled to a single monocarboxylic acid by an amide bond to yield a product with a free amino group. This —$NH_2$ group is then coupled to the —COOH of the desacylsaponins' 3-O-glcA using the carbodiimide method. The end product is a desacylsaponin with a fatty acid added at the 3-O-glcA residue.

The following are general protocols for forming fatty acid-desacylsaponin conjugates of the present invention.

i) Formation of the fatty acid-diamine product:

A fatty acid, such as caprylic or arachidonic acid, can be activated to its N-hydrosuccinimide (NHS) ester by reacting with NHS and dicyclohexylcarbodiimide (DCC) in an alcohol, such as ethanol, dimethylformamide (DMF), or other convenient organic solvent. The reaction, carried out with mixing in the dark at 0 to 4° C., has for each mole of fatty acid about one mole of DCC and 1.5 to 2.0 moles of NHS. After a 4–6 hours of reaction, the precipitated dicyclohexylurea is removed by filtration, and the filtrate is added to an organic solvent containing a diamine in a 5 to 10-fold molar excess relative to the fatty acid. The diamine is preferably ethylenediamine or propylenediamine. The reaction is allowed to proceed with mixing in the dark at 0 to 4° C. for about 8 hours. The product, a diamine coupled to a single fatty acid residue by a stable amide bond, can be separated from the other reactants by selective extraction, precipitation, and/or chromatography.

Another procedure for the preparation of a fatty acid-diamine is the mixed anhydride technique: Arachidonic acid and tri-n-butylamine are dissolved in dioxane, using about 2 moles of the amine for each mole of the acid. To the cooled solution isobutylchlorocarbonate (one mole per mole of fatty acid) is added by mixing, and is reacted for 0.5 to 1 hour. This mixture is added in one portion to dioxane containing 8 to 10 times a molar excess of diamine a nd allowed 4 hours to react with stirring and cooling. The fatty acid-diamine can be extracted, and separated by precipitation and/or chromatography. The modified fatty acid is used for addition to the desacylsaponins.

ii) Addition of the fatty acid-diamine product to desacylsaponins:

The carboxyl of the desacylsaponins' 3-O-glcA residue is activated by the carbodimide procedure as described above. The reaction, carried out in DMF, dioxane or other polar solvent, has for each mole of desacylsaponin about one mole of DCC and 1.5 to 2.0 moles of NHS. The reaction is carried out in the dark at 0 to 4° C. for 4–6 hours, and the precipitated dicyclohexylurea is removed by filtration. The filtrate is added to a DMF or dioxane solution containing the fatty acid-diamine product in approximately equimolar amount with respect to the desacylsaponins; and is thereafter reacted at 25° C. for about 8 hours. The product, a conjugate consisting of a desacylsaponin having a fatty acid residue added to the 3-O-glcA residue, is separated by differential extraction, precipitation, and/or chromatography. The isolated conjugate is dissolved in water and lyophilized.

Terpenoid-Desacylsaponin Conjugates

Terpenes have structural characteristics somewhat similar to the acyloil acyl groups from Quillajasaponins. Thus, terpenes and compounds derived from terpenes (terpenoids) are suitable lipophilic molecules to conjugate to the desacylsaponins' 3-O-glcA residue. Useful terpenoids include a functional group that is capable of reacting with either the desacylsaponin or a bifunctional linker. Typical functional groups with this property that are found in terpenoids include alcohol, aldehyde and ketone functionalities. Retinal, a vitamin A aldehyde that has an important role in immunity, is an example of such a compound. A single diamine molecule is coupled to one of Retinal, yielding a Retinal with a free amino group. This product is added to the desacylated saponin using the carbodiimide method.

i) Formation of the Retinal-diamine product:

To a methanolic solution containing Retinal and a 1 0-fold molar excess of ethylenediamine, is added sodium cyanoborohydride dissolved in methanol. The reaction is allowed to proceed for about 8 hours to reduce the reversible Schiff bases to a stable alkylamine bond. The pH is adjusted if needed with an organic acid such as acetic or trifluoroacetic acid. The Retinal-diamine product is recovered by selective solvent extraction, precipitation and/or crystallization.

ii) Addition of the Retinal-diamine product to desacylsaponins:

The carboxyl of the desacylsaponins' 3-O-glcA residue is activated by the carbodiimide procedure described above. The reaction, carried out in DMF, dioxane or other suitable solvent, has for each mole of desacylsaponin 1 mole of DCC and 1.5 to 2.0 moles of NHS. After reacting in the dark at 0 to 4° C. for 4–6 hours, the precipitated dicyclohexylurea is removed by filtration. The filtrate is added to DMF or dioxane containing the Retinal-diamine product in an equimolar amount with respect to the desacylsaponins, and the mixture is allowed to react at 25° C. for about 8 hours. The product, a desacylsaponin containing a Retinal residue added to the 3-O-glcA residue, is separated by solvent extraction, precipitation, and/or chromatography. The isolated neo-saponin is dissolved in water and lyophilized.

Aliphatic Amine-desacylsaponin Conjugates

Aliphatic groups from an amine can be added to Quillaja desacylsaponins by coupling the amino group to the —COOH of the 3-O-glcA residue forming an amide bond. The carboxyl of the desacylsaponins' 3-O-glcA residue is activated by the carbodiimide procedure described above. The reaction, carried out in DMF, dioxane or other solvent, has for each mole of desacylsaponin about one mole of DCC and 1.5 to 2.0 moles of NHS. This mixture is allowed to react in the dark at 0 to 4° C. for 4–6 hours, and the precipitated dicyclohexylurea is removed by filtration. The filtrate is added to a DMF or dioxane solution containing the aliphatic amine in an equimolar amount with respect to the desacylsaponins; and allowed to react at 25° C. for about 8 hours. The product, a desacylsaponin conjugated to an aliphatic chain via the 3-O-glcA residue of the desacylsaponin, is separated by differential extraction, precipitation, and/or chromatography. The isolated conjugate is dissolved in water and lyophilized.

Glycosyl-fatty Acid:Desacylsaponin Conjugates

Figure 1B:
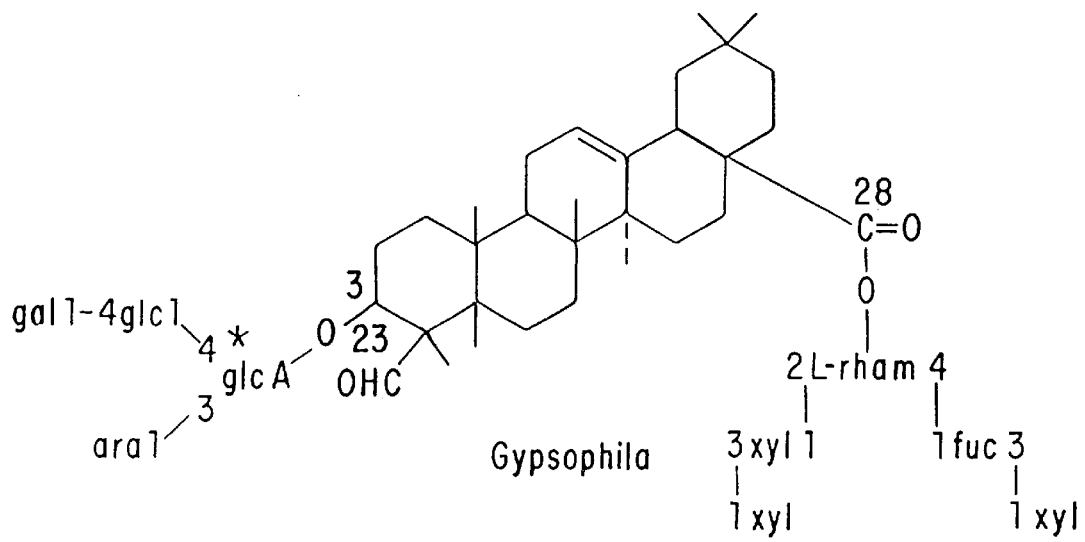
Figure 1C:
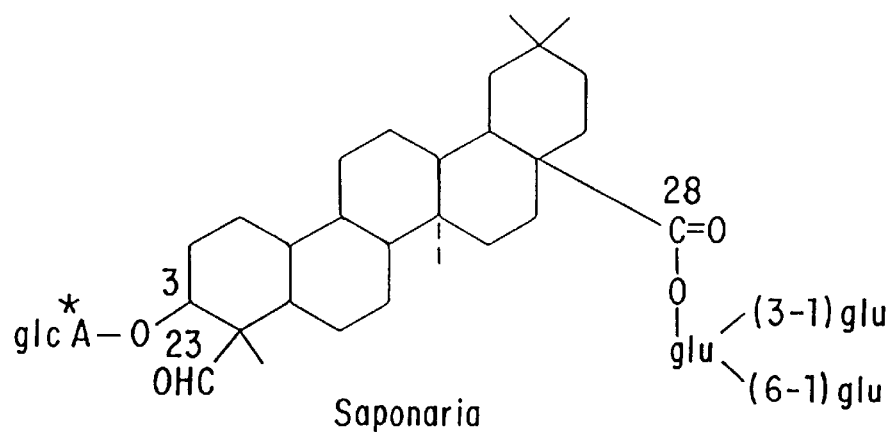

One of the acyloil acyl moieties of Quillaja saponins is linked to a disaccharide to form the structure [5-O-α-rhamnopyranosyl-(1→2)-α-L-arabinofuranosyl-3,5-dihydroxy-6-methyl-octanoyl]-3,5-dihydroxy-6-methyl-octanoyl]. This structure is linked by an ester bond to the C3-hydroxyl group of the fucopyranosyl residue (FIG. 1). Thus, another chemical modification is a conjugate having a glycosylated lipophile added to the 3-O-glcA residue of desacylsaponins.

i) Preparation of the glycosylated fatty acid:

A fatty acid containing an alcohol group, such as the unsaturated ricinoleic acid, dissolved in dry acetone, is mixed with tosyl chloride dissolved in acetone. While stirring the reaction mixture, pyridine or triethylamine is added to neutralize the liberated HCl. The tosyl chloride converts the hydroxyl group into an active sulfonate. The sulfonate is separated from the other reactants by extraction or other adequate procedure. The active sulfonate is mixed with glucosamine in DMF, or other appropriate solvent, at pH 9.5. Sulfonates are good leaving groups that, after reaction with the glucosamine's amino group, will form stable linkages between the amine and the initial —OH group-carrying carbon. Other good leaving groups that are known in the art may be substituted for the sulfonates. The glucosamine-ricinoleic acid product is recovered by extraction, precipitation, or other procedure. This product is activated by the carbodiimide method and reacted with a diamine, in a manner equivalent to that described above for the formation of fatty acid-diamine product.

ii) Addition of glucosamine-ricinoleic acid product to desacylsaponins:

The glucosamine-ricinoleic acid conjugate carrying a free amine group, introduced by reacting with a diamine using the carbodiimide method, is allowed to react with the desacylsaponin using again the carbodiimide reaction or the mixed anhydride method, both as described above for the addition of fatty acid-diamine product to desacylsaponins. The resulting conjugate is recovered by extraction, precipitation, and/or chromatography. The conjugate is dissolved in water and lyophilized. This conjugate consists of glucosamine-ricinoleic acid covalently linked to the 3-O-glcA residue of the desacylsaponin.

Quillajasaponin Conjugates having a Hydrophobic/hydrophilic Side-chain

A side-chain with amphipathic characteristics, i.e. asymmetric distribution of hydrophilic and hydrophobic groups, facilitates (a) the formation of micelles as well as an association with antigens, and (b) the accessibility of the triterpene aldehyde to cellular receptors. It is also possible that the presence of a negatively-charged carboxyl group in such a side-chain may contribute to the repulsion of the triterpene groups, thus allowing them a greater degree of rotational freedom. This last factor would increase the accessibility of cellular receptors to the imine-forming carbonyl group.

Saponin Analogue with a Charged Hydrophobic-hydrophilic Side-chain i) Reaction of N-octyl-monoxyethylene with epichlorohydrin:

To 0.05 moles (9.9 ml) of N-octyl-monooxyethylene dissolved in 50 ml of dimethylformamide (DMF), add with stirring 1 equivalent (0.05 moles) of pentane-washed NaH to form an alkoxide. Add with stirring the alkoxide solution to 35 ml of DMF plus 0.2 moles (15.6 ml) of epichlorohydrin. React at <60° C., and follow the reaction by TLC. Stop the reaction by an addition of 250 ml of water. Extract the aqueous solution 3 times with 90 ml of methylene chloride reach time in order to partition the activated N-octyl-monooxyethylene. Dry the pooled organic solvent phase over magnesium sulfate, and remove the solvent in a rotary evaporator. The syrupy residue is the activated product (11). Check purity by TLC; if needed, purify by chromatography on silica gel (see Scheme 4).

ii) Addition of 2-amino-3-mercaptopropionic acid (cysteine) to n-octyl-monooxyethylene:

Prepare a fresh solution of epoxylated n-octyl-monooxyethylene by dissolving the syrupy residue (11) (<0.05 moles) in 30 ml of 0.2 M potassium phosphate buffer, pH 7.8–8.4, in 50% DMF. Add (11), in small aliquots and with stirring, to 0.10 moles (12.10 gm) of L-cysteine freshly dissolved in 60 ml of the 0.2 M potassium phosphate buffer, pH 7.8–8.4, in 50% DMF. If needed, adjust the pH of the cysteine solution to pH 7.8–8.4 with either 1 M KOH or 1M phosphoric acid. Let react overnight at 35–40° C. with moderate stirring under a nitrogen atmosphere. Concentrate by rotary evaporation and extract with toluene, or if soluble, with chloroform, the n-octyl-monooxyethylene cysteinyl derivative (12) (mol. wt. 351.34). The cysteine excess and other salts should remain in the aqueous phase, or precipitate in the organic solvent. Filter the organic phase, and extract twice with water to remove any potassium phosphate. Dry the organic phase over magnesium sulfate. If it is necessary to remove excess cysteine, or to change solvents (for instance: from toluene to chloroform) use chromatography on silica gel. Remove solvent by rotary evaporation, product (12) should be a syrupy residue. Check its purity by TLC on silica gel or HPLC against (11) and cysteine (see Scheme 4).

iii) Activation of quillaja saponin glucuronic acid:

To 0.4 gm (240 μmoles) of desacylated quillajasaponins dissolved in 10 ml of DMF/pyridine (60:40, v/v), add 480 μmoles (100 mg) of dicyclohexylcarbodiimide (DCC) and 480 μmoles (56 mg) of N-hydroxysuccinimide (NHS). Let the reaction proceed with mixing overnight at room temperature. (Protect from humidity). Add an additional 50 mg of DCC and 28 mg of NHS, and continue reaction for another hour. Cool the reaction to ~0–4° C. for an hour and filter through a very fine glass filter to remove the insoluble DCC byproduct dicyclohexylurea. Remove pyridine in a rotary evaporator, and add 40 ml of cold ethyl acetate (EtOAc) to precipitate the DS-saponin:NHS derivative (13). After 1–2 hours in a freezer, collect the precipitate derivative by filtration on a fine glass filter paper, and wash the ppt on the filter paper with additional EtOAc. Product (13) can be stored under vacuum over strong dessicant (see Scheme 5).

iv) Linking of the activated DS-saponin to the hydrophobic/hydrophilic side-chain:

Dissolve the DS-saponin:NHS derivative (13) (assume 100% yield ~240 μmoles) in ~5 ml of DMF/pyridine (60:40, v/v). To the solution of (13) add 0.20 gm (~0.5 mole) of the derivative (12) dissolved in 5 ml of pyridine to yield a ~2-fold molar excess over (13). Protect from moisture and let react for 8–12 hours at room temperature to yield the saponin analog with a n-octyl-monooxyethylene cysteinyl side-chain (14). Check the reaction progress by TLC using n-butanol-pyridine-water, 3:2:1, as a solvent, and iodine or charring for detection. In a rotary evaporator remove the pyridine from the reaction mixture, add ~30 ml of cold EtOAc, and store in a freezer for 3–5 hours to precipitate (14). Collect precipitate (14) by filtering on a fine glass filter paper, and wash the precipitate with EtOAc to remove residual (12) which should be soluble in EtOAc. If needed purify (14) by chromatography on silica gel. Dissolve the saponin analog in water, and lyophilize it. Analyze (14) by HPLC, and confirm by mass spectrometry (see Scheme 6).

Saponin Analogue with an Uncharged Hydrophobic-hydrophilic Side-chain

The synthesis of a quillajasaponin analogue having an uncharged side-arm has steps (1) and (3) in common with the synthesis described above. Steps (2) and (4) are quite similar and are described here.

i) Addition of ethylenediamine to n-octyl-monooyethylene:

Dissolve the syrupy residue (11, prepared according to step i, above) (>0.05 moles) in 30 ml of acetonitrile 0.2 N potassium carbonate. Add (11) in small aliquots and with stirring to 0.40 moles (26.7 ml) of ethylenediamine dissolved in 60 ml of 0.2 M piperazine-0.2 N potassium carbonate. Run the reaction at room temperature overnight with stirring. Neutralize with HCl, concentrate by rotary evaporation and dissolve the N-octyl-monooxyethylene ethylenediamine derivative (15) (mol. wt. 332.30) preferably in chloroform, otherwise in toluene. (The ethylenediamine-.HCl may be insoluble in the organic solvents, particularly if it is hydrated.) If ethylenediamine.HCl is insoluble in the organic solvent, filter through a fine glass filter, and extract the organic phase with water to remove the residual ethylenediamine. Dry the organic phase by adding dried magnesium sulfate to it. In the event that ethylenediamine cannot be removed by solvent extraction, or if the solvent needs to be changed (such as from toluene to chloroform), use chromatography on silica gel. Remove solvent in a rotary evaporator. Product should be a syrupy residue. Check its purity by TLC or HPLC against (11) and ethylenediamine (see Scheme 6).

ii) Linking of the activated DS-saponin to the hydrophobic/hydrophilic side-chain:

Dissolve the DS-saponin:NHS derivative (13, prepared according to step iii, above) (assume 100% yield ~240 μmoles) in ~5 ml of DMF/pyridine (60:40, v/v). Add to (13) 0.33 gm (1 mmole) of derivative (15) dissolved in 5 ml of pyridine to yield a ~4-fold molar excess over (13). Let react for 8–12 hours at room temperature (protect from moisture) to yield the saponin analog with a N-octyl-monooxyethylene ethylenediamine side chain (16). Check progress of reaction by TLC or HPLC. In a rotary evaporator remove the pyridine from the reaction mixture, add ~30 ml of cold EtOAc, and store in a freezer for 3–5 hours to precipitate (16). Collect precipitate (16) by filtering on a fine glass filter paper, and wash the precipitate with EtOAc to remove residual (15) which should be soluble in EtOAc. If needed, purify (16) by chromatography on silica gel. Dissolve the saponin analog in water, and lyophilize it. Analyze (16) by HPLC, and confirm by mass spectrometry (see Scheme 7).

iii) General:

Toluene can be removed by rotary evaporation under reduced pressure ($bp_{760}$ 110.6° C.). DMF can be removed by rotary evaporation under reduced pressure ($bp_{39}$ 76° C., $bp_{3.7}$ 25° C.).

The N-octyl-monooxyethylene derivatives of 2,3-diaminopropionic acid and ethylendiamine should be soluble in several organic solvents, such as alcohols, ketones, and aromatic solvents, but insoluble in petroleum ether. During extraction of organic phases with water, there is a possibility of formation of emulsions due to the detergent properties of the N-octyl-monoethylene derivatives. These emulsions can be broken by either warming the suspension, or centrifuging.

Saponin analogs should be insoluble in EtOAc, alcohols such as ethanol and isopropanol and acetone.

Addition of Lipophile Groups to Related Triterpene Saponins

As indicated earlier, the non-acylated triterpenoid saponins from Gypsophila and Saponaria have a significant adjuvant effect on the secondary immunoresponse. However, different from Quillajasaponins, their effects on the primary immunoresponse are minor. It is contemplated that addition of a fatty acid moiety to these saponins will improve their adjuvanticity during the early primary immunoresponse. Strong circumstantial evidence for the proposed role of the fatty acid groups in the unique adjuvanticity of Quillajasaponins is provided by QS-7, one of these saponins (Kensil, C. et al., *J. Immunol.* 146:431 (1991); Kensil et al., U.S. Pat. No. 5,057,540 (1991)). This saponin which is very hydrophilic has (a) a retention time comparable to that of desacylated Quillaja saponins, and (b) lacks an arabinose which is the glycosyl residue associated with the Quillajasaponins' acyloyl acyl moiety. These characteristics strongly suggest that QS-7 is non-acylated. This saponin also has different activities from the acylated Quillaja saponins: QS-7 is non-toxic, non-hemolytic, resembling the behavior of desacylated Quillajasaponins. While QS-7 enhances humoral immunity, its effects on antibody isotype profile are different from those observed with QS-21. These properties suggest that the acyloil moiety is responsible for the unique adjuvanticity, as well as the toxicity observed with the other Quillajasaponins. Thus, addition of an appropriate lipophile moiety to non-acylated adjuvant saponins is expected to enhance their adjuvant effects on the humoral and cell-mediated immunity, as well as limit the toxicity observed with Quillaja saponins. The latter is a crucial requirement for the successful application of these adjuvants to pediatric vaccines.

The adjuvant and immunostimulating properties of some saponins apparently have certain structural requirements, including (a) a triterpene aglycone with an aldehyde group linked or attached to position 4, and (b) branched sugar chains at positions 3 and/or 28 of the aglycone. The role of the triterpene group could be to facilitate binding to the cholesterol in cell membranes, with some subsequent involvement of the aldehyde group. Branched sugar chains appear to be important for the stimulation of humoral immunity, as indicated by the lack of adjuvanticity of quillajasaponins modified by periodate oxidation.

It has been postulated that Quillajasaponins' adjuvanticity may require a close saponin:antigen association, and that their acyl groups facilitate this association by enhancing their hydrophobicity. It has also been shown that increasing the number of quillajasaponin molecules associated with a saponin conjugated to a protein results in enhanced adjuvanticity. Apparently, the quillajasaponin molecules are being held together by hydrophobic interactions between their acyl moieties forming a micelle-like structure. Comparison of the Quillajasaponins' adjuvanticity with that of the non-acylated saponins from *Gypsophila oldhamiana* and *Saponaria officinalis* have showed somewhat similar activities. However, Quillajasaponins elicit a much higher primary immunoresponse (Bomford, R. et al., *Vaccine* 10:572 (1992)). This finding suggests that the Quillajasaponins' hydrophobic acyl moieties enhance the intrinsic adjuvant properties of their desacylsaponins.

A comparison of the structures of saponins from Quillaja, Gypsophila, and Saponaria, shows several similarities (FIG. 1). All of them have triterpene aglycones with an aldehyde group in position 23, branched oligosaccharides linked by an ester bond in position 28, and a 3-O-glucuronic acid (3-O-glcA) that in Quillaja and Gypsophila is linked to branched oligosaccharides. However, Quillajasaponins are the only ones with acyloyl acyl moieties. Structure/function studies of Quillajasaponins have shown that the presence of the 23-aldehyde group, the integrity of the oligosaccharide chains, and the 28-O-acyl groups are critical for full adjuvanticity. The 3-O-glcA residue apparently can be modified without the loss of adjuvanticity. Indeed, the 3-O-glcA glycoside residue has been used to conjugate Quillajasaponins to antigens (Kensil, C. et al., *Vaccines* 92:35 (1992)). Comparison of the adjuvant activities for these saponins shows that Quillajasaponins induce a significantly better primary immunoresponse, but, that all of them induce strong secondary immunoresponses (Table I). This differential effect suggests a major role for the Quillajasaponins' acyloil acyl residues in the primary immunoresponse. The significantly lower primary immunoresponse induced by the Quillaja's desacylsaponins, as compared to those induced by its acylated saponins, provides support for this proposed role.

TABLE I

| Acylated | Quillaja sap.* | Gypsophila sap. | Saponaria sap. |
| --- | --- | --- | --- |
| | + | – | – |
| Antibody response (log end point) | | | |
| Primary | 5.45 | 2.14 | 1.86 |
| Secondary | 8.66 | 9.13 | 6.71 |

*Quillaja saponins have an 28-O-acyloyl-acyl moiety linked to fucose.

Modifications of the Gypsophila and Saponaria saponins can be carried out in a fashion similar to that described earlier for Quillaja desacylsaponins, using the carboxyl of the 3-O-glcA residue as the site for addition of new moieties to the saponins. These neo-saponins with a new lipophile moiety in their structures should have better adjuvant properties than the original saponin molecules.

Figure 2A:
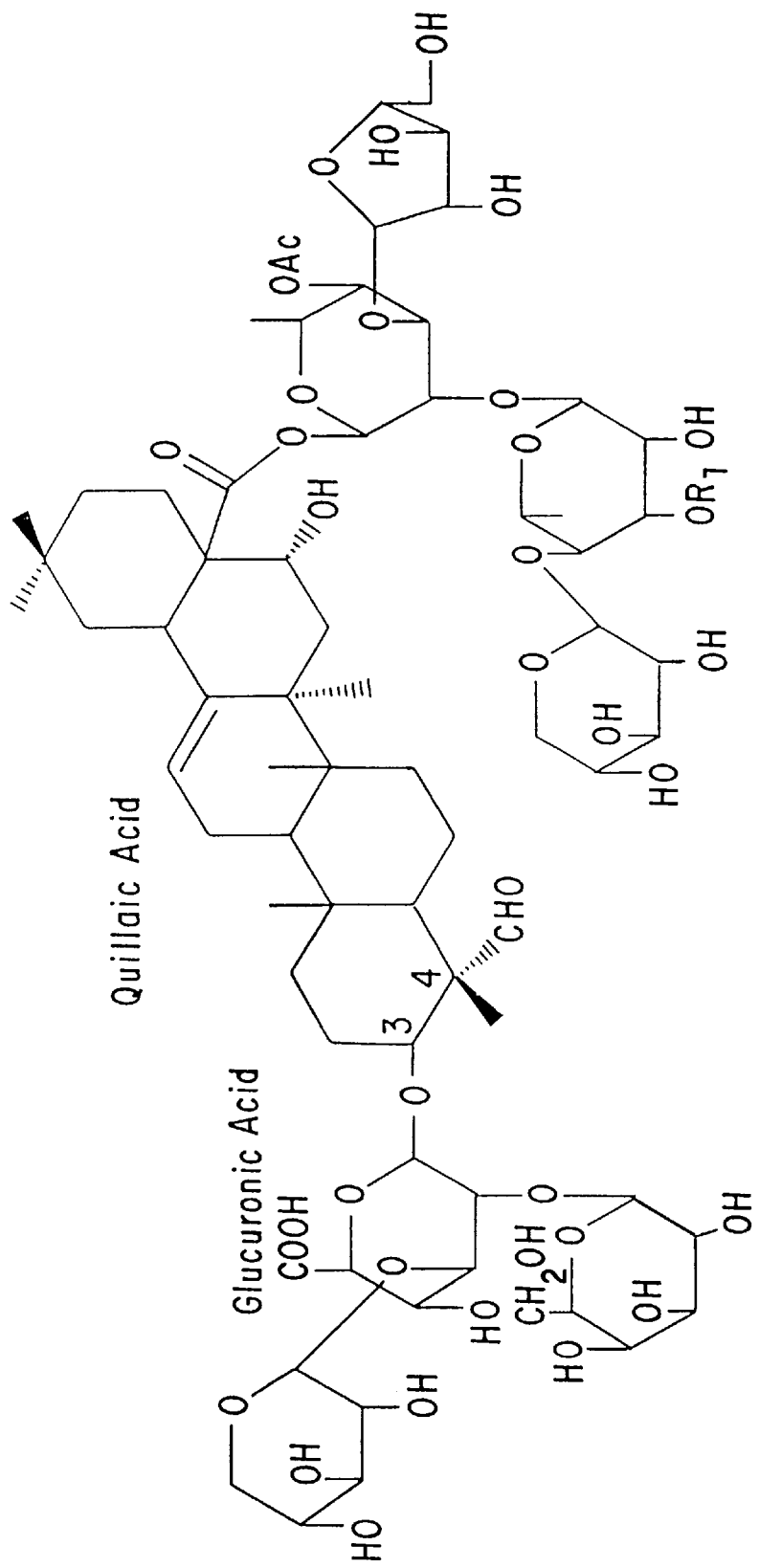
FIG. 2 illustrates representative chemical structures for (a) saponin from *Acanthophyllum squarrosum* and (b) lucyoside P.
Figure 2B:
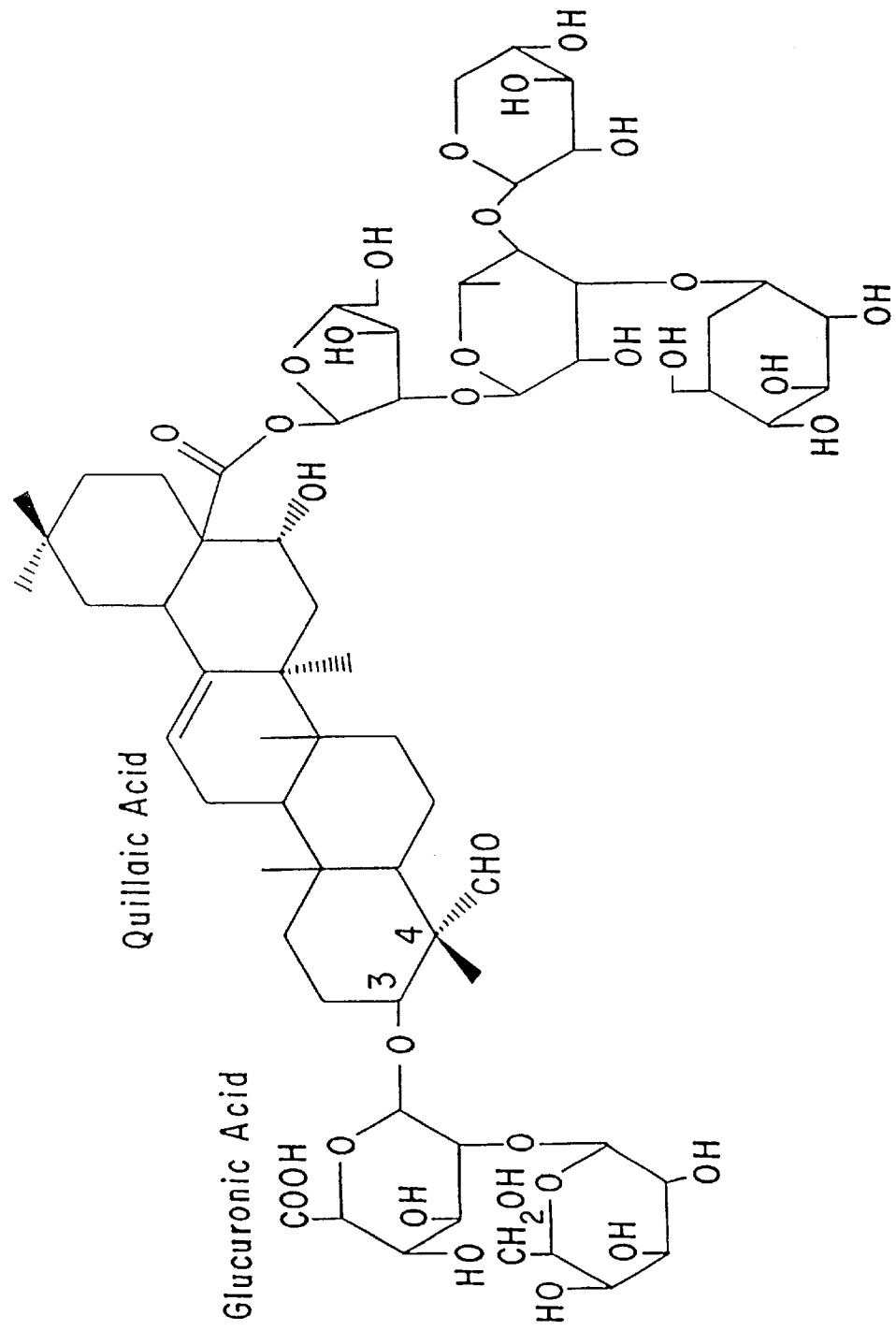
Figure 3:
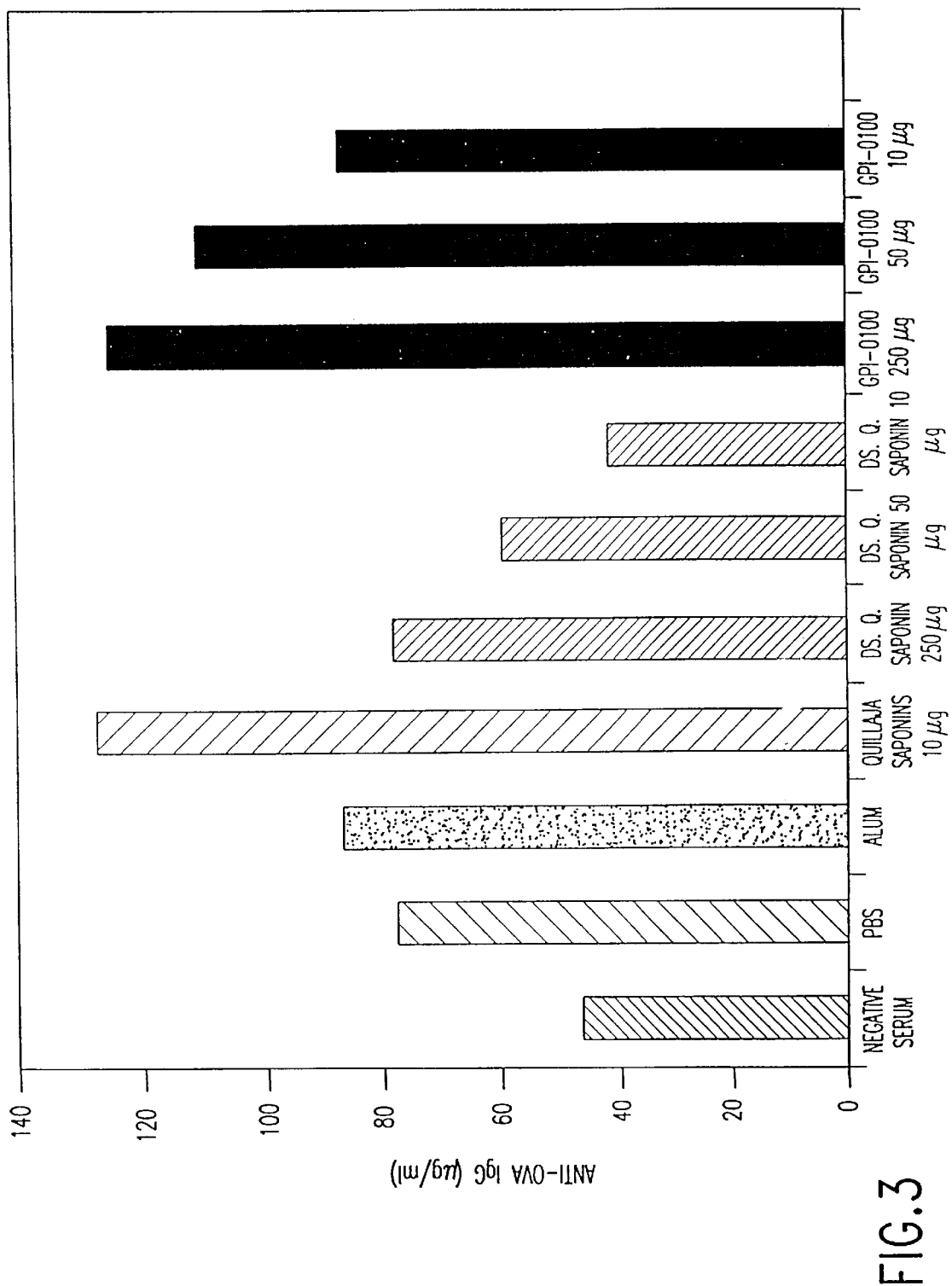
FIG. 3 demonstrates the comparison of the anti-OVA IgG primary immune response elicited by OVA alone, and in the presence of alum, quillaja saponin, and different doses of desacylated quillaja saponin, and of a quillaja saponin-lipophile conjugate (GPI-0100), Example 3 of the present invention.
Figure 4:
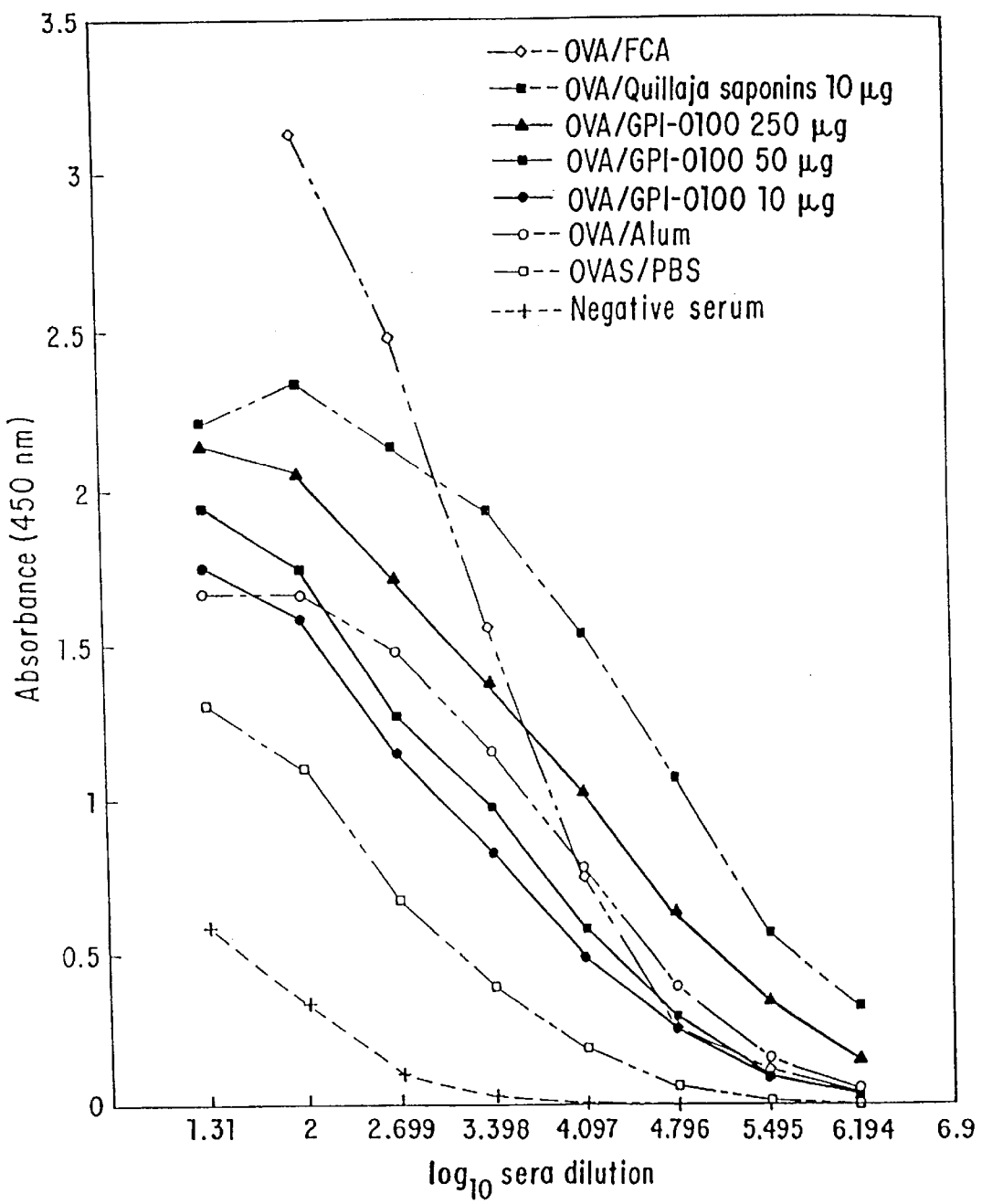
FIG. 4 shows the typical end point titers for immunization with the OVA antigen in the presence of Freund's complete adjuvant, quillaja saponin, quillaja saponin-lipophile conjugate of the present invention, alum, and OVA alone. Absorbance due to the antigen-specific antibody binding was plotted as a function of the logarithm of the sera dilution.
Figure 5:
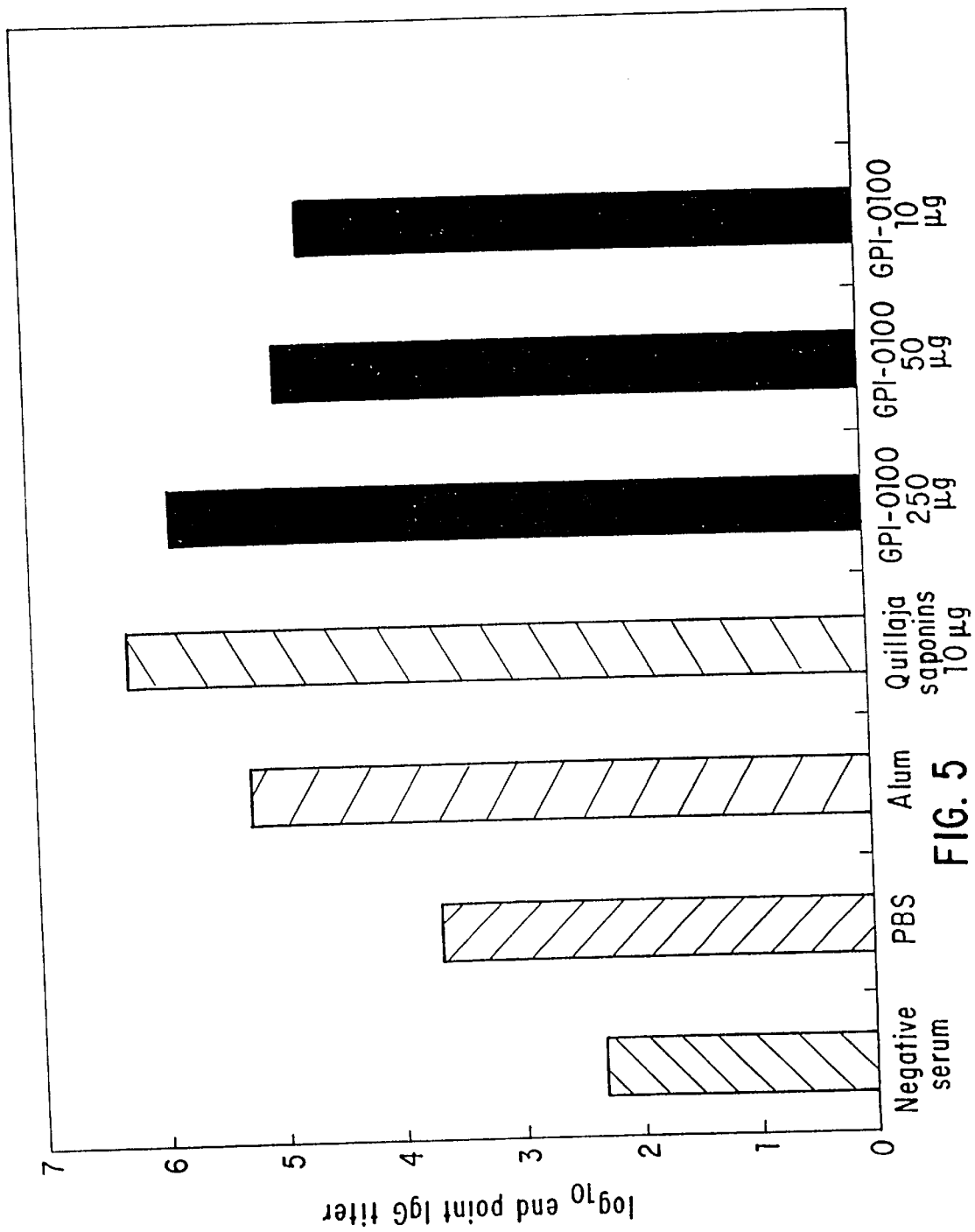
FIG. 5 demonstrates the comparison of the log end point titers for the secondary anti-OVA IgG immune response elicited by OVA alone, and in the presence of alum, quillaja saponin, and various doses of quillaja saponin-lipophile conjugate (GPI-0100).
Figure 6:
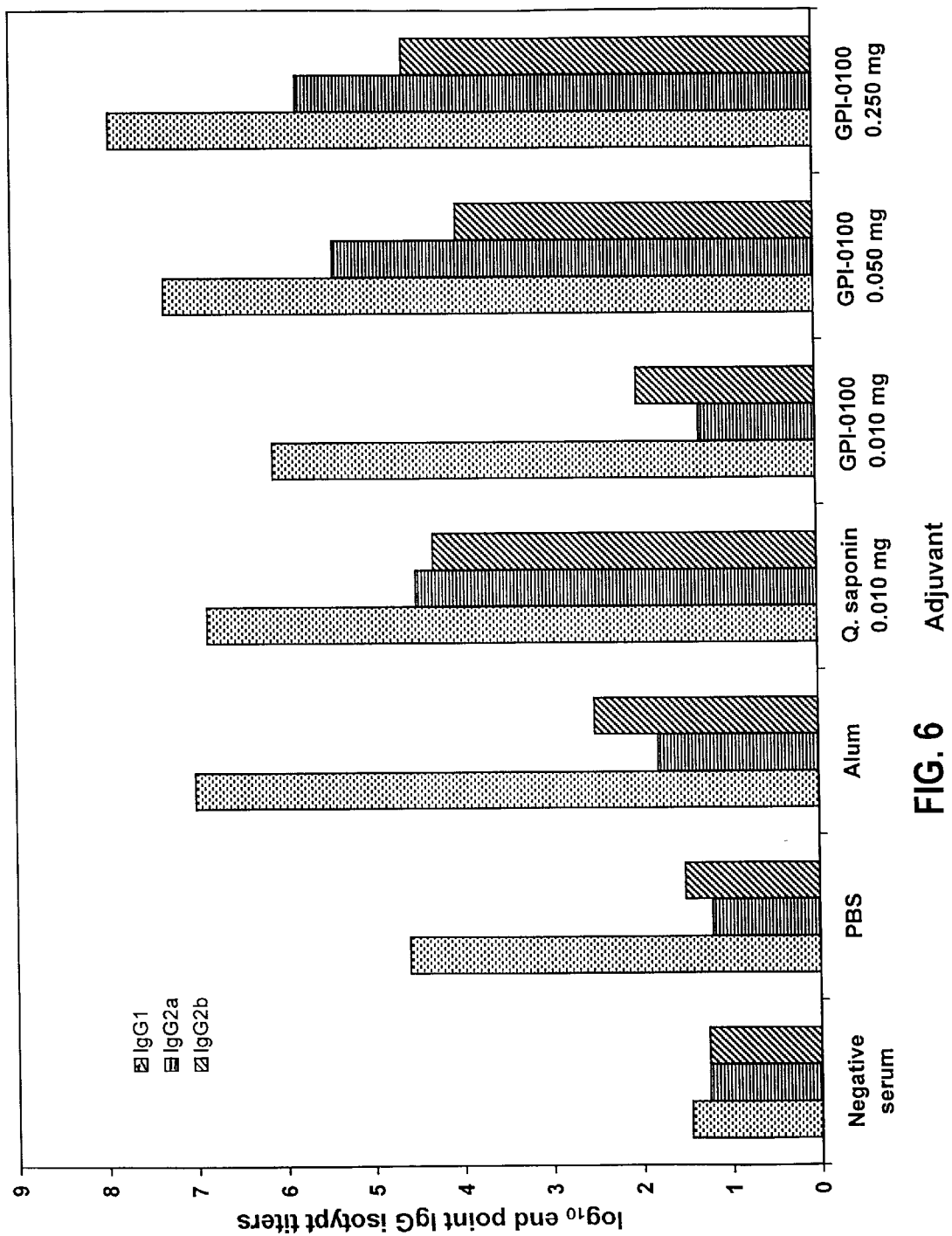
FIG. 6 shows the effects of alum, quillaja saponin, and different doses of quillaja saponin-lipophile conjugate of the present invention (GPI-0100), on the production of IgG isotypes. The log end point titers were determined using antibodies specific for each isotype.

Other non-acylated triterpene saponins, such as squarroside A, lucyoside P and *S. jenisseensis* desacylated saponin, also have the structural requirements for adjuvanticity and immunostimulating properties. For instance, it has been shown that the saponin squarroside A (FIG. 2) has immunomodulating activity, as measured by an in vitro lymphoproliferative test. Thus, these saponins can be modified by addition of lipophilic chains to their 3-O-glucuronic acid residue to produce neo-saponins with improved adjuvant properties.

Methods of Use

Immune adjuvants are compounds which, when administered to an individual or tested in vitro, increase the immune response to an antigen in a subject to which the antigen is administered, or enhance certain activities of cells from the immune system. Some antigens are weakly immunogenic when administered alone or are toxic to a subject at concentrations that evoke useful immune responses in a subject. An immune adjuvant can enhance the immune response of the subject to the antigen by making the antigen more strongly immunogenic. The adjuvant effect can also result in the ability to administer a lower dose of antigen to achieve a useful immune response in a subject.

Immune adjuvants can modify or "immunomodulate" the cytokine network, up-regulating the immune response. Concomitant with this immunomodulation there is also a selection of which T-cell, Th1 or Th2, will mount this immune response. Th1 responses will elicit complement fixing antibodies and strong delayed-type hypersensitivity reactions associated with IL-2, IL-12, and γ-interferon. Induction of CTL response appears to be associated with a TH1 response. Th2 responses are associated with high levels of IgE, and the cytokines IL-4, IL-5, IL-6 and IL-10. The aldehyde-containing saponins induce a strong Th1 response. However, some of their analogs may induce a Th2 response.

The immunogen-inducing activity of compounds and compositions of the present invention can be determined by a number of known methods. The increase in titer of antibody against a particular antigen upon administration of a composition of the present invention can be used to measure immunogenic activity. (Dalsgaard, K. *Acta Veterinia Scandinavica* 69:1–40 (1978)). One method requires injecting CD-1 mice intradermally with a test composition that includes one or more exogenous antigens. Sera is harvested from mice two weeks later and tested by ELISA for anti-immunogen antibody.

Compositions of the invention are useful as vaccines to induce active immunity towards antigens in subjects. Any animal that may experience the beneficial effects of the compositions of the present invention within the scope of subjects that may be treated. The subjects are preferably mammals, and more preferably humans.

The invention also provides a method of inducing an immunological response in a subject to one or more pathogens, comprising administering to the subject a vaccine as described above.

The invention further provides a method of inducing a protective immune response in a subject, sufficient to prevent or attenuate an infection by a pathogen, comprising administering to the subject a composition comprising nucleic acid fragments and an adjuvant of the present invention.

The vaccines of the present invention may be used to confer resistance to infection by either passive or active immunization. When the vaccines of the present invention are used to confer resistance to infection through active immunization, a vaccine of the present invention is administered to an animal to elicit a protective immune response which either prevents or attenuates an infection. When the vaccines of the present invention are used to confer resistance to infection through passive immunization, the vaccine is provided to a host animal (e.g., human, dog, or mouse), and the antisera elicited by this antisera is recovered and directly provided to a recipient suspected of having an infection caused by a member of the genus.

The present invention thus concerns and provides a means for preventing or attenuating an infection resulting from organisms which have antigens that are recognized and bound by antisera produced in response to the immunogenic polypeptides included in vaccines of the present invention. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of pathogenic infection. The prophylactic administration of the vaccine(s) serves to prevent or attenuate any subsequent infection. When provided therapeutically, the vaccine(s) is provided upon or after the detection of symptoms which indicate that an animal may be infected with a pathogen or have a certain cancer. The therapeutic administration of the vaccine(s) serves to attenuate any actual infection. Thus, the vaccines, may be provided either prior to the onset of infection (so as to prevent or attenuate an anticipated infection) or after the initiation of an actual infection.

Saponin-lipophile conjugates can be employed as a sole adjuvant in vaccines of the present invention, or alternatively, can be administered together with non-saponin adjuvants. Such non-saponin adjuvants useful with the present invention include oil adjuvants (for example, Freund's Complete and Incomplete), liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), polymers (for example, non-ionic block polymers, non-ionic surfactants, polyphosphazenes, cyanoacrylates, polymerase-(DL-lactide-co-glycoside), among others, and certain natural substances (for example, lipid A and its derivatives, wax D from *Mycobacterium tuberculosis*, as well as substances found in *Corynebacterium parvum*, *Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the non-saponin adjuvant may comprise a protein fragment comprising at least the immunostimulatory portion of the molecule. Other known immunostimulatory macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3,3'-dicarboxylic acid and 4-nitro-2-aminobenzoic acid (See Sela, M., *Science* 166:1365–1374 (1969)) or glycolipids, lipids or carbohydrates.

The saponin-lipophile conjugate employed in vaccines of the present invention exhibit adjuvant effects when administered over a wide range of dosages and a wide range of ratios to one or more particular antigens being administered.

The saponin-lipophile conjugates can be administered either individually or admixed with other substantially pure adjuvants to achieve an enhancement of immune response to an antigen. The saponin-lipophile conjugates can be a substantially pure modified saponin, or can be in the form of a mixture of saponins-lipophile conjugates.

The saponin lipophile conjugates of the present invention can be utilized to enhance the immune response to one or more antigens. The antigen can be proteins, peptides, polysaccharides, or mixtures thereof. The proteins and peptides may be purified from a natural source, synthesized by means of solid phase synthesis, or may be obtained means of recombinant genetics. The antigen may comprise a protein fragment comprising one or more immunogenic regions of the molecule. Typical antigens suitable for the immune-response provoking compositions of the present invention include antigens derived from a variety of pathogens, including: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, or tuberculosis; or protozoans, such as *Babeosis bovis* or Plasmodium.

The adjuvants of the present invention can be employed in combination with one or more bacterial antigens from a particular bacteria. Bacteria for which vaccines can be formulated include: Helicobacterpylori, *Chlamydia pneumoniae, Chlamydia trachomatis, Ureaplasma urealyticum, Mycoplasma pneumoniae*, Staphylococcus spp., *Staphylococcus aureus*, Streptococcus spp., *Streptococcus pyogenes, Streptococcus pneumoniae, Streptococcus viridans, Enterococcus faecalis, Neisseria meningitidis, Neisseria gonorrhoeae, Bacillus anthracis*, Salmonella spp., *Salmonella typhi, Vibrio chlorea, Pasteurella pestis, Pseudomonas aeruginosa*, Campylobacter spp., *Campylobacter jejuni*, Clostridium spp., *Clostridium difficile*, Mycobacterium spp., *Mycobacterium tuberculosis*, Treponema spp., Borrelia spp., *Borrelia burgdorferi*, Leptospria spp., *Hemophilus ducreyi, Corynebacterium diphtheria, Bordetella pertussis, Bordetella parapertussis, Bordetella bronchiseptica, hemophilus influenza, Escherichia coli*, Shigella spp., Erlichhia spp., and Rickettsia spp.

Bacterial antigens can be native, recombinant or synthetic immunogenic polypeptides, or peptide fragments. Such bacterial antigens include, but are not limited to, selectins or lectins from bacteria that bind to carbohydrate determinants present on cell surfaces; and bacteria receptors for proteins, such as fibronectin, laminin, and collagens.

The adjuvants of the present invention can be employed in combination with one or more antigens from a particular virus to form a vaccine. Viruses for which vaccines can be formulated include: Influenza viruses, Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease virus.

Viral antigens can be native, recombinant or synthetic. Such viral antigens include, but are not limited to, viral proteins that are responsible for attachment to cell surface receptors to initiate the infection process, such as (i) envelope glycoproteins of retroviruses (HIV, HTLV, FeLV and others) and herpes viruses, and (ii) the neuramidase of influenza viruses. Additionally, peptides derived from such viral proteins can be employed, either free, or associated non-covalently, or conjugated covalently to a suitable carrier.

Tumor associated antigens can be native, recombinant or synthetic immunogenic polypeptides or peptide fragments. Such tumor associated antigens include, but are not limited to, killed tumor cells and lysates thereof, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, MUC-1 and peptide fragments thereof, CA 125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, truncated epidermal growth factor receptor (EGFR), and chimeric protein $p210^{BCR-ABL}$.

Peptides that are derived from these tumor associated antigens can be employed, either free, or non-covalently associated, or conjugated covalently to a suitable carrier. Alternatively, gangliosides can be employed, either free, non-covalently associated or conjugated covalently to a suitable carrier; or oligosaccharide sequences that are specific or predominantly found in cancer cells can be employed either free, non-covalently associated or conjugated covalently to a suitable carrier.

The vaccines of the present invention are suitable for use with many types of antigens, including peptide antigens. It is presently possible to produce synthetic antigens which mimic the antigenically significant epitopes of a natural antigen by either chemical synthesis or recombinant DNA technology. These have the advantage over prior vaccines such as those based on attenuated pathogens of purity, stability, specificity and lack of pathogenic properties which in some cases can cause serious reaction in the immunized subject. The vaccines of the invention may be used with any form of antigen, including those capable of acting as vaccines by themselves and those which require formulation with an effective adjuvant.

Preferred immunogenic peptides of synthetic or recombinant origin contain e.g., from 8–50, preferably from 10–30 amino acid units. The antigen may e.g., mimic one or more B cell, or B cell and T cell epitopes of a pathogenic organism, so that the vaccine elicits both neutralizing antibodies and a T cell response against the organism (see, for example, the disclosure of synthetic antigens to MIV in WO88/10267 and WO97/13909).

Alternatively, the peptide may elicit an immune response against another biologically active substance, particularly a substance having hormonal activity. An example in the latter category would be the induction of an immune response against endogenous luteinizing hormone-releasing hormone (LHRH). Such treatment can e.g., be used for suppression of sex steroid hormone levels for the treatment of androgen- and oestrogen-dependent carcinomas and in the immuno-castration of farm and domestic animals (see GB-B-2196969).

Polypeptides that are useful in the present invention include antigenic polypeptides or epitope-bearing fragments thereof combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Trauneckeretal., *Nature* 331:84–86 (1988)). Fusion proteins that have a disulfide-linked dimeric structure due to the IgG part can also be more efficient in binding and neutralizing other molecules than the monomeric protein or protein fragment alone (Fountoulakis et al., *J. Biochem.* 270:3958–3964 (1995)).

Any of the aforementioned polypeptides orpeptides may be modified with additional chemical groups present at their amino and/or carboxy termini, such that, for example, the stability, bioavailability, and/or immunogenic activity of the peptides is enhanced. For example, hydrophobic groups such as carbobenzoxy, dansyl, or t-butyloxycarbonyl groups, may be added to the peptides' amino termini. Likewise, an acetyl group or a 9-fluorenylmethoxycarbonyl group may be placed at the peptides' amino termini. Additionally, the hydrophobic group t-butyloxycarbonyl, or an amido group may be added to the peptides' carboxy termini.

In one preferred embodiment, carrier proteins, such as keyhole limpet hemocyanin, ovalbumin, BSA or tetanus toxoid are added (conjugated) to the peptide. In some cases it may be desirable to link the peptide to a carrier to boost its immunogenicity. Suitable carriers are well known in the art, e.g., protein carriers such as purified protein derivative of tuberculin (PPD), tetanus toxoid, cholera toxin and its B subunit, ovalbumin, bovine serum albumin, soybean trypsin inhibitor, muramyl dipeptide and analogues thereof, and a cytokine or fraction thereof. When using PPD as the carrier, a higher titre of antibodies is achieved if the recipient of the vaccine is already tuberculin sensitive, e.g., by virtue of earlier BCG vaccination. Methods for coupling immunogenic peptides or polypeptides to such macromolecular carriers are disclosed in Harlow et al., *Antibodies: A Laboratory Manual*, 2nd Ed.; Cold Spring Harbor Laboratory Press, Cold Spring Harbor, N.Y. (1988), the entire disclosure of which is incorporated by reference herein.

The saponin conjugates of the present invention can be utilized to enhance the immune response against antigens produced by the use of DNA vaccines. The DNA sequences in these vaccines coding for the antigen can be either "naked" or contained in a delivery system, such as liposomes. Typical vaccines using this approach are viral vaccines, such as influenza, herpes, cytomegalovirus, HIV-1, HTLV-1, FIV, cancer vaccines, and parasitic vaccines. The saponin conjugates can be administered together with the DNA or at an earlier and/or later time than the DNA administration.

DNA vaccines are currently being developed for a number of infectious diseases. Boyer, J., et al., *Nat. Med.* 3:526–532 (1997); reviewed in Spier, R., *Vaccine* 14:1285–1288 (1996). Such DNA vaccines contain a nucleotide sequence encoding one or more antigenic polypeptides oriented in a manner that allows for expression of the subject polypeptide.

In a DNA or RNA vaccine, a polynucleotide operatively coding for an immunogenic polypeptide in a pharmaceutically acceptable administrable carrier is administered in vivo into a tissue of a mammal suffering from cancer or pathogenic infection, wherein the polynucleotide is incorporated into the cells and a therapeutically effective amount of an immunogenic polypeptide is produced in vivo. The DNA or RNA formulation may further comprise a cationic vehicle such as cationic lipids, peptides, proteins, or polymers, and are preferably administered into muscle tissue. The tissue may also be skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, or connective tissue. Circular DNA molecules are preferred as they will persist longer than single-stranded polynucleotides, and they will be less likely to cause insertional mutation by integrating into the target genome.

The polynucleotide material delivered to the cells in vivo can take any number of forms. It may contain the entire sequence or only a fragment of an immunogenic polypeptide gene. It may also contain sequences coding for other polypeptide sequences. It may additionally contain elements involved in regulating gene expression (e.g., promoter, enhancer, 5' or 3' UTRs, transcription terminators, and the like). The polynucleotide may also comprise an immunostimulatory sequence that would enhance the immunogenicity of a given gene product, and/or it may comprise sequences that would enhance the delivery of the polynucleotide, such as by increasing cellular and/or nuclear uptake. Techniques for obtaining expression of exogenous DNA or RNA sequences in a host are known. See, for example, Korman et al., *Proc. Nat. Acad. Sci. (USA)* 84:2150–2154 (1987), which is hereby incorporated by reference.

Thus, the vaccines present invention can also employ genetic fusions wherein the nucleic acid sequences coding antigenic sequences are linked to additional nucleic acid sequences to produce fusion proteins. These fusion proteins encoded by the nucleic acid sequences may include epitopes of pathogenic or non-pathogenic origin designed to produce proteins having enhanced immunogenicity. Further, the fusion proteins may contain antigenic determinants known to provide helper T-cell stimulation, peptides encoding sites for post-translational modifications which enhance immunogenicity (e.g., acylation), peptides which facilitate purification, or amino acid sequences which target the fusion protein to a desired location (e.g., a heterologous leader sequence).

Cancer cells often have distinctive antigens on their surfaces, such as truncated epidermal growth factor, folate binding protein, epithelial mucins, melanoferrin, carcinoembryonic antigen, prostate-specific membrane antigen, HER2-neu, which are candidates for use in therapeutic cancer vaccines. Because tumor antigens are normal or related to normal components of the body, the immune system often fails to mount an effective immune response against those antigens to destroy the tumor cells. To achieve such a response, quillajasaponin and saponin-lipophile conjugates can be utilized. Triterpenoid saponin adjuvants containing an aldehyde work by reacting with amino groups of the receptor protein(s) present on certain T-cells, and forming Schiff bases. As a result of this reaction, exogenous proteins are allowed to enter the pathway for processing endogenous antigens, leading to the production of cytolytic or cytotoxic T cells (CTL). This unique adjuvant effect induces the production of antigen specific CTLs which seek and destroy those tumor cells carrying on their surface the tumor antigen(s) used for immunization. The saponin conjugates of the present invention can also be used with carbohydrate tumor antigens, such as gangliosides, the Thomsen-Friedenreich (T) antigen, and others.

The vaccines of the present invention may be co-administered to an animal with an immune system modulator (e.g., CD86 and GM-CSF).

The present invention further provides multi-component vaccines, comprising a plurality of antigenic polypeptides, or fragments thereof, together with one or more saponin-lipophile conjugates and a pharmaceutically acceptable diluent, carrier, or excipient, wherein the polypeptide(s) are present in an amount effective to elicit an immune response to a pathogen in an animal. Polypeptides may further be combined with one or more immunogens of other organisms to produce a multi-component vaccine intended to elicit an immunological response against members of the a particular genus and, optionally, one or more other organisms.

Heterogeneity in the composition of a vaccine may be provided by combining polypeptides. Multi-component vaccines of this type are desirable because they are likely to be more effective in eliciting protective immune responses against multiple species and strains than single polypeptide vaccines. Thus, as discussed in detail below, a multi-component vaccine may contain one or more, preferably 2 to about 20, more preferably 2 to about 15, and most preferably 3 to about 8, polypeptides, or fragments thereof.

Multi-component vaccines are known in the art to elicit antibody production to numerous immunogenic components. Decker, M. and Edwards, K., *J. Infect. Dis.* 174:S270–275 (1996). In addition, a hepatitis B, diphtheria, tetanus, pertussis tetravalent vaccine has recently been demonstrated to elicit protective levels of antibodies in human infants against all four pathogenic agents. Aristegui, J., et al., *Vaccine* 15:7–9 (1997).

A multi-component vaccine can also be prepared using techniques known in the art by combining one or more polypeptides, or fragments thereof, with additional non-pathogenic components (e.g., diphtheria toxin or tetanus toxin, and/or other compounds known to elicit an immune response).

The saponin-lipophile conjugates of the present invention can also be administered alone to potentiate the immune system for treatment of chronic infectious diseases, especially in immune compromised patients. Examples of infectious diseases for which conjugates of the present invention can be employed for therapeutic or prophylactic treatment are described in U.S. Pat. No. 5,508,310. Potentiation of the immune system by saponin conjugates can also be useful as a preventative measure to limit the risks of nosocomial and/or post-surgery infections.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the saponin/antigen conjugates may be administered over a wide range of dosages and a wide range of ratios to the antigen being administered. The initial dose may be followed up with a booster dosage after a period of about four weeks to enhance the immunogenic response. Further booster dosages may also be administered.

The saponin-lipophile conjugates of the present invention may be employed in such forms as capsules, liquid solutions, emulsions, suspensions or elixirs for oral administration, or sterile liquid forms such as solutions, emulsions or suspensions. Any inert carrier is preferably used, such as saline, or phosphate-buffered saline, or any such carrier in which the compounds used in the method of the present invention have suitable solubility properties for use in the methods of the present invention.

The saponin-lipophile conjugates of the present invention can be employed in association with liposomes, wherein the saponin can be in one or both of the bilayers of the liposome, loosely-associated with lipid material in a liposome preparation (where the conjugates are not within a bilayer, but otherwise associated with lipids), in some instances, entrapped within the bilayers of the liposomes. See, for example, U.S. Pat. No. 4,235,877 to Fullerton.

The invention also provides for a kit for the immunization of an individual comprising a carrier compartmentalized to receive in close confinement therein one or more container means wherein a first container contains a saponin-lipophile conjugate of the invention. The kit may also include at least one other container means which contains a saponin adjuvant or other adjuvant as described herein.

Addition of Biotinyl group to Related Triterpene Saponins

As earlier indicated, biotinylated saponin analogs are useful reagents for identifying and determining which cells of the immune system have receptors capable of reacting with imine-forming saponins. These saponins (such as those from quillaja, gypsophila, and saponaria) replace the co-stimulatory ligand B7.1 that is expressed on APCs and react with CD28 receptor on T-cells. Upon co-stimulation with B7.1 or an imine-forming saponin adjuvant, T-cells are activated to form antigen-specific CTLs. The use of these tagged saponin analogs allows for the determination of the progress of the immune response process by qualitatively or quantitatively measuring the presence of T-cells that have cell surface receptors that can bind to desacylated or non-acylated saponins.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Preparation of Quillaja Desacylsaponins (4)

The required triterpene saponin starting materials can be obtained from commercial preparations of *Quillaja saponaria* Molina saponins, which are acylated. By way of example, two kinds of commercial preparations can be used:
 (a) Quillaj a saponins (practical grade, obtained from Fisher Scientific), contain approximately 25% (w/w) of saponins and 75% (w/w) of water-soluble contaminants, i.e., oligosaccharides, tannins, etc.; and
 (b) Dialyzed Quillaja saponins or Quil A (obtained from Accurate Chemicals or Sigma Chemical Co.) are >80% (w/w) saponins with a methanol insoluble contaminant(s).

Practical grade Quillaja saponins can be further purified as follows:

A. Practical grade saponin preparation (1) is dissolved in water to a concentration of 20–25% (w/v) and the pH is adjusted to about 4 with 1N acetic acid to form a cloudy solution. The cloudy solution is poured into a standard dialysis sack and dialyzed against 3–4 changes of 25–50 volumes of water for 24 hours. Water is changed every 4–8 hours of dialysis. The dialysate is then lyophilized, yielding a white colored preparation. After dialysis, the saponin preparation (2) contains a contaminant (perhaps pigments or tannins) which is insoluble in methanol. Yield: ±25% of the initial weight of the practical grade saponin preparation, which represents about 95% (w/w) of the original saponins.

B. One gm of dry saponin preparation (2) is extracted with 50 ml of methanol at 60° C. for 20–25 minutes. The suspension is filtered and undissolved material is re-extracted with 30 ml of methanol at 60° C. for 20–25 minutes. The clear methanolic filtrates are pooled and brought to dryness with a rotoevaporator. The methanol-extracted saponin preparation (3) is free of methanol-insoluble contaminant(s). Yields are up to 70% of preparation (2).

The acyl groups of Quillaja saponins are removed by mild alkaline hydrolysis to yield four distinct desacylsaponins (two being isomers), plus 3,5-dihydroxy-6-methyloctanoic acid, and 3,5-dihydroxy-6-methyloctanoic acid 5-O-α-L-rhamnopyranosyl-(1→2)-α-arabinofuranoside. By way of example, the following alkaline hydrolysis methods are useful in preparing these desacylated saponins (4).

(i) Methanol extracted saponins (3) (60 mg/ml) are boiled with 6% $Na_2CO_3$ in 50% methanol for 1 hour, and the reaction mixture neutralized with Dowex 50W-X8 $H^+$ (a synthetic, strongly-acidic cation exchanger that is a sulfonated polystyrene-divinylbenzene resin) and filtered. The filtrate is concentrated with a rotoevaporator, and partitioned between ethyl acetate and water. The aqueous phase will include most of the desacylsaponins, whereas the organic EtOAc phase will contain most of the octanoic acids. The EtOAc is removed from the aqueous phase by passing nitrogen gas or using a rotoevaporator, and the aqueous desacylsaponin solution (4) is lyophilized.

(ii) Methanol extracted saponins (3, 0.1 gm) are resuspended in 3 ml of 90% n-propanol. This suspension/solution is adjusted to 0.5N NaOH by addition of a 5N NaOH stock solution and mixed for 2 hours at room temperature (20–25° C.). The suspension is centrifuged 5 minutes at 50×g to yield a lightly colored supernatant, which is discarded, and a brownish grainy precipitate. The precipitate is washed three times by resuspending it with 3 ml of 90% n-propanol and centrifuging at 50×g. The resulting pellet of desacylsaponins (4) is redissolved in 3 ml water and lyophilized.

Alternatively, methanol extracted saponins (3) are dissolved in water to form a solution having 20 mg/ml saponins and the solution is adjusted to a final concentration of 0. 15M triethylamine, pH 12. After one hour at 40–50° C., the alkaline hydrolysis is terminated by adding acetic acid to pH 7.0. The reaction mixture is extracted with ethyl acetate to remove triethylamine and some hydrolysis products. The desacylsaponins (4) should remain in the aqueous phase. Another procedure is to dissolve 1 g of (3) in 30 ml of methanol, add 50 ml of 7 N methanolic ammonia, stir the solution for 5 hours at room temperature, and remove the ammonia under a stream of nitrogen. The aqueous solution is extracted with 80 ml of ethylacetate, and the organic phase is discarded. The aqueous phase containing the desacylsaponins is frozen and lyophilized.

EXAMPLE 2
Purification of Saponin from Gypsophyla sp.

A 5% solution of crude gypsophyla saponin in 10 mM acetic acid is dialyzed in a dialysis sack having a molecular weight cut-off of ~12,000 Daltons against 20 volumes of 10 mM acetic acid at 4° C. The acetic acid solution is changed two times after 4 hours. (This step removes polysaccharide and some small molecular weight contaminants). The dialized solution is concentrated in a rotoevaporator and lyophilized. One gram of the dialyzed gypsophyla saponin is extracted twice with 50 ml of pure methanol (MeOH) at room temperature for 24 hours each and filtered. If there is undissolved material, extract once with 50 ml of MeOH:water (40/60) at room temperature, and filter to remove insoluble matter. Filtrates are pooled and concentrated at ~40° C. in a rotoevaporator to yield a syrupy saponin extract (I). Dissolve the extract in water to yield a 5% saponin solution, and extract this solution twice with 0.5 volume of ethyl acetate. The aqueous phase is submitted to chromatography on Fractogel TSK HW-40F, eluting with a gradient of 0 to 50% (v/v) of MeOH in water containing 0.05 M $Na_2CO_3$. Samples were analyzed by TLC on silica gel using n-butanol:acetic acid:water (4/1/5) as a solvent, and the saponin visualized with the Liebermann:Burchard reaction. Alternatively, the saponin from (I) can be precipitated by adding 5 volumes of ethyl acetate, and fractionated by silica gel chromatography using chloroform:MeOH:water (64:40:8) as a solvent. Analogs of gypsophyla saponin can be prepared using the same procedures developed for the desacylated quillaja saponins.

EXAMPLE 3
Addition of Aliphatic Amine to Desacylsaponin via Carboxyl Group of Glucuronic Acid A $C_6$–$C_{20}$ aliphatic amine, preferably a $C_9$ or $C_{12}$ aliphatic amine, can be added to the carboxyl of the glucuronic acid residue of desacylsaponins (4) to yield conjugated desacylsaponins (5) using the carbodiimide method. Either DCC (dicyclohexylcarbodiimide), or water-soluble EDC (1-ethyl-3-(3-dimethylaminopropyl)carbodiimide, with or without NHS (N-hydroxysuccinimide) or water-soluble sulfo-NHS, can be used. The reaction is carried out in organic solvents, such as dioxane, DMF (dimethylformamide), THF (tetrahydrofuran), DMSO (dimethylsulfoxide), alcohols and pyridine, alone or in mixtures anhydrous or with water. The presence of water is dictated by the solubility properties of the Quillaja desacylsaponins, which can be soluble in 50% methanol, 50% n-propanol, aqueous DMSO, and DMF, as well as anhydrous THF or dioxane, and other solvents with similar properties.

(i) One-step method using dodecylamine (a) To 100 mg (60 μmoles) of desacylsaponins (4) dissolved in 1 ml of 50% n-propanol, is added i ml of a 0.6M dodecylamine solution (600 μmoles) in 50% n-propanol. The pH is then adjusted to between 5 and 7 with 3N phosphoric acid. 600 μmoles of dry EDC (95 mg) is stirred into the resulting solution and mixed for 6–8 hours (0° C. to 10° C.). An additional 300 μmoles (47 mg) of EDC is added, and the reaction is allowed to proceed overnight at 0° C. to 10° C. The reaction can be stopped by removing the free alkylamine with a Dowex 50 type resin. (The resin may also remove the acyl urea from EDC.) The resin is removed by filtration. The filtrate containing the conjugated desacylsaponins (5) is mixed with 5 volumes of n-propanol to precipitate (5). The precipitate is collected, dissolved in water, dialyzed and lyophilized.

(b) If the desacylsaponins are soluble in anhydrous pyridine, alone or with anhydrous THF, the reaction can be carried out with DCC. 100 mg of (4) (60 μmoles) are dissolved in pyridine and/or THF, using no less than 1 ml but no more than 5 ml. 1 ml of a 0.3M dodecylamine solution (300 μmoles) in pyridine and/or THF is thereafter added to the reaction mixture, followed by 300 μmoles of dry DCC. The mixture is allowed to react with mixing overnight at 0° C. to 10° C. During the reaction, insoluble dicyclohexylurea is formed; this is removed by centrifugation. The supernatant containing the conjugated desacylsaponins (5) is diluted with 10 volumes of EtOAc to precipitate (5). The EtOAc containing the free alkyl amine, residual DCC, and the pyridine and/or THF is discarded. Precipitate is washed with EtOAc, dissolved in water and re-extracted with EtOAc before removing the EtOAc and lyophilizing.

(ii) Two-step method using dodecylamine (a) To 100 mg (60 μmoles) of desacylsaponins (4) dissolved in 1 ml of 50% n-propanol is added 0.2 ml of a 0.6M dodecylamine solution (120 μmoles) in 50% n-propanol. The pH of the mixture is adjusted to pH 5–7 with 3N phosphoric acid (carboxylic acids are to be avoided). 120 μmoles of dry EDC (10 mg) and 120 μmoles sulfo-NHS (26 mg) are added to the reaction mixture with stirring and the reaction is allowed to proceed overnight at 0° C. to 10° C. Five volumes of n-propanol are added to precipitate the conjugated desacylsaponins (5). The precipitate is collected, dissolved in water, dialyzed and lyophilized.

(b) If desacylsaponins are soluble in anhydrous pyridine alone or mixed with anhydrous THF, the reaction can be carried out with DCC. 100 mg of (4) (60 μmoles) are dissolved in pyridine and/or THF, using no less than 1 ml but no more than 5 ml of solvent. 0.4 ml of a 0.3M dodecylamine solution (120 μmoles) in pyridine and/or THF is added to the desacylsaponin solution, followed by 120 μmoles of dry DCC and 120 μmoles of dry NHS. The mixture is allowed to react with mixing overnight at 0° C. to 10° C. Insoluble dicyclohexylurea is formed, which is removed by centrifugation. The supernatant containing the conjugated desacylsaponins (5) is diluted with 10 volumes of EtOAc to precipitate (5) and to remove the free alkyl amine, residual DCC, and NHS. The precipitate is dissolved in water and extracted with EtOAc before concentration with a roto-evaporator and lyophilization. Modification is confirmed by mass spectra.

Another preferred embodiment of the invention is one in which two or more hydrophobic chains are introduced at the carboxyl group of the 3-O-glucuronic acid residue of a desacylated or non-acylated saponin. This addition of multiple lipophilic chains can be made using different chemical approaches, including those described below. Preferably, a molecule that includes two or three lipophilic side-chains is covalently attached to the 3-O-glucuronic acid, either directly or via a bifunctional linker.

EXAMPLE 4
Addition of Phosphatidylethanolamine Dipalmitoyl to Desacylsaponin To 0.35 gm (210 mmoles) of desacylsaponins (4) dissolved in 3 ml of anhydrous DMF/pyridine (60:40, v/v) at room temperature, is added 280 mmoles of phosphatidylethanolamine fatty acid derivative (dipalmitoyl, distearoyl, and others) in DMF/pyridine. To this reaction mixture is added with mixing 400–600 mmoles of dry DCC (0.08–0.125 gm) and 400 mmoles of dry NHS (0.05 gm) and allowed to react with mixing for 12–16 hours at rt. The reaction mixture is cooled to 4° C. for an hour and filtered to remove insoluble dicyclohexylurea, a DCC byproduct. To the filtrate containing the conjugated desacylsaponins is added 10 volumes of cold ethanol to precipitate the conjugated desacylsaponins and to remove residual DCC, NHS, and free phosphatidylethanolamine fatty acid derivative. After 2–4 hours at 0–4° C., the precipitated saponin conjugate is collected by filtration. The precipitate is washed on the filter paper with 10–20 ml of ethyl acetate. The precipitated saponin conjugates are then dissolved in 10 ml. of water, and this solution is extracted with 1 volume of ethyl acetate. The ethyl acetate is removed from the aqueous solution using a rotoevaporator, and the sample is lyophilized.

EXAMPLE 5
Addition of L-2,4-diaminobutyric Acid Dimyristoyl to Desacylsaponin To 0.63 gm (2.5 mmoles) of myristoyl chloride dissolved in 25 ml of acetonitrile, is added 2.10 gm (11 mmoles) of 2,4-diaminobutyric dihydrochloride, plus 2.00 gm potassium carbonate. The mixture is reacted with stirring for 12–16 hours at 65° C. The reaction mixture is thereafter dried under reduced pressure, and the residue is dissolved in ethyl acetate, extracted with water, and again extracted with water saturated with magnesium sulfate. The organic phase is dried over anhydrous magnesium sulfate. The magnesium sulfate is removed by filtration. The filtrate is dissolved under reduced pressure, and the purity of the compound is checked by silica gel TLC. If needed, the dimyristoyl derivative is purified by chromatography on silica gel.

To 0.40 gm, (240 mmoles) of desacylsaponins (4) dissolved in 5 ml of anhydrous DMF/pyridine (60:40, v/v) at room temperature is added 2 ml of DMF/pryidine containing 0.23 gm of dimyristoyl derivative. Thereafter, 480–720 mmoles of dry DCC (0.10–0.15 gm) and 480 mmoles of dry NHS (~0.06 gm) are added with mixing, and allowed to react with mixing for 12–16 hours at room temperature. The reaction mixture is cooled to 4° C. for an hour and filtered to remove insoluble dicyclohexylurea, a DCC byproduct. To the filtrate containing the conjugated desacylsaponins is added 10 volumes of cold ethanol to precipitate the conjugated desacylsaponins and to remove residual DCC, NHS, and free dimyristoyl derivative. After 2–4 hours at 0–4° C., the precipitated saponin conjugate is collected by filtration. The precipitate is washed on the filter paper with 20–30 ml of ethyl acetate. The precipitated saponin conjugate is dissolved in 20 ml of water, and the solution is extracted with 1 volume of ethyl acetate. The ethyl acetate is removed from the aqueous solution using a rotoevaporator and is lyophilized. The sample purity is checked by silica gel TLC. If necessary, the conjugated desacylsaponin can be purified by chromatography on silica gel.

EXAMPLE 6
Addition of Citric Acid-tripalmitoyl to Desacylsaponin

To 0.50 gm (2.5 mmoles) of citric acid dissolved in 20 ml acetonitrile or pyridine is added with mixing 3.60 gm (15 mmoles) of 1-hexadecylamine. To this solution is added 35 mmoles of dry DCC (7.20 gm) and 35 mmoles of NHS (4.00 gm), and allowed to react overnight at rt. The reaction mixture is cooled to 4° C. for an hour and is filtered to remove insoluble dicyclohexylurea. Solvent is removed under reduced pressure in a rotoevaporator. The dry residue is dissolved in alcohol and the residual alkylamine is removed with a strongly acidic resin (Dowex 50). The purity of the product is checked by silica gel TLC. If necessary, the product is purified by chromatography on silica gel. The citric acid-tripalmitoyl derivative (1.87 gm, 2 mmoles) is dissolved in 20 ml of acetonitrile, and 2.5 mmoles of 1,1'-carbonyldiimidizole (CDI) (0.40 gm) is added and the mixture is allowed to react for 4 hours at rt under anhydrous conditions. A 5-fold excess of ethylene diamine (10 mmoles ~0.65 ml) is then added to the reaction mixture and allowed to react for another 2–3 hours at rt. Thereafter, 10% water is added to destroy residual CDI, and solvent is removed under reduced pressure. The reaction products are dissolved in a suitable solvent, e.g. methanol or chloroform, and purified by silica gel chromatography. Fractions containing the aminated citric acid-tripalmitoyl derivative (M.W. ~1019.7) are pooled, and solvent is removed under reduced pressure.

The desacylated saponin conjugate is prepared by reacting in pyridine/DMF (40:60, v/v) 1 mole of desacylsaponin with 1.5 moles of the aminated citric acid-tripalmitoyl derivative using the DCC/NHS method described before. After filtration to remove the insoluble dicyclohexylurea, the conjugated saponin is precipitated with several volumes of ethyl acetate, re-dissolved in water and lyophilized.

EXAMPLE 7
Preparation of Saponin Analogs having Steroid or Triterpenoid Moieties The disclosed invention is not limited to linear hydrophobic chains as the lipophilic moiety. Non-aromatic and aromatic cyclic and heterocyclic compounds, such as triterpenoids and steroids can also be employed as the lipophilic moiety. As an example, the preparation of a steroid derivative is described here. To 2 mmoles of deoxycholic acid (0.79 gm) in 10 ml of pyridine, is added with mixing 10 mmoles (0.67 ml) of ethylenediamine, followed by 4 mmoles of dry DCC (0.82 gm) and 4 mmoles of NHS (0.50 gm). The mixture is allowed to react overnight at 25° C. The reaction is then cooled and the insoluble DCC byproduct is filtered, and solvent is removed under reduced pressure. The products are dissolved in a small volume of chloroform-methanol (3:2, v/v) or similar solvent, and the aminated product is separated from the ethylenediamine by chromatography on silica gel. The solvent is removed under reduced pressure.

The desacylated saponin conjugate is prepared by reacting 1 mole of desacylsaponin with 2 moles of the aminated deoxycholic acid derivative using the DCC/NHS method described above. The conjugated saponin is precipitated with alcohol, re-dissolved in water and lyophilized.

EXAMPLE 8
Testing for Adjuvant Effect Using Ovalbumin (OVA) as Antigen

Adjuvant effect can be assessed by increase in antigen-specific antibody titers due to addition of potential adjuvant in the immunization formulation. Increased titers result from increased antibody concentrations and/or increased antigen/antibody affinity. Adjuvant effects of saponins have previously been measured by increase in titer of neutralizing antibodies to foot-and-mouth disease vaccines in guinea pigs (Dalsgaard, K., Archiv. fur die gesamte Virusforschung 44:243–254 91974)), increase in titer of precipitating antibodies to BSA (as measured by radial immunodiffusion) in guinea pigs vaccinated with BSA/saponin mixtures (Dalsgaard, K., Acta Veterinaria Scandinavica 69:1–40 (1978)), as well as by the increase in titer of anti-keyhole limpet hemocyanin (KLH) antibody (measured by ELISA) in mice immunized with KLH/saponin (Scott et al. Int. Archs. Allergy appl. Immun. 77:409–412 (1985)).

Assessment of adjuvant effect can be determined by increase in anti-OVA antibody following immunization with OVA/saponins, OVA/desacylated saponin s or OVA/saponin analogs, compared with immunization with OVA in the absence of saponin. The adjuvant activity in the saponin conjugate fraction is measured as follows: CD2F1 mice (8–10 weeks old) are immunized intradermally with the following formulation: 20 µg OVA (Sigma) and adjuvant of the present invention or quillajasaponin (at doses ranging from 10–2500 µg), or quillaja saponin (at a dose of 10 µg) in 200 µl PBS. The two immunizations are given at two-week intervals. Control mice are injected with either PBS or PBS with OVA, plus 200 µg of aluminum hydroxide. Sera is harvested two weeks post-immunization. Anti-OVA antibody is determined by ELISA: Immulon II plates were coated overnight at 4° C. with 100 µl of an OVA solution (10 mg/ml in PBS) in rows, A, C, E, and G. Plates are washed twice with PBS. Nonspecific binding is prevented by incubating for 1.5 h at 37° C. with 100 µl diluent (2% casein acid hydrolysate (Oxoid, w/v) in PBS) per well in all wells. Plates are washed four times with 0.05% Tween 20 surfactant in distilled water. Sera at dilutions of 1:20, 1:100, 1:500, 1:2500, 1:12,500, 1:62,500, 1:312,500 and 1:1,562,500 is incubated in rows A+B, C+D, E+F and G+H, respectively (100 µl/well) for 1 h at room temperature. Plates are washed as described above. Boehringer-Mannheim horse radish peroxidase conjugate goat anti-mouse antibody (1/5000 in 5% OVA in diluent) is incubated for 30 min at room temperature (100 µl per well, all wells). Plates are washed as described above. The extent of peroxidase reaction is determined by reaction with 2,2'-azido-bis(3-ethylbenzthiazoline)-6-sulfonate (30 minute reaction at room temperature, absorbance measured at 450 nm) or with 3,3',5,5'-tetramethylbenzidine (10 min. reaction of nonspecific antibody binding to the total antibody binding is removed by subtraction of the absorbance of the antigen-negative well from the absorbance of the antigen-positive well for each sera dilution. The IgG produced during the primary immune response is determined by interpolating the absorbance values obtained with a 1:20 serum dilution in a calibration curve. The calibration curve is constructed using known amounts of an anti-OVA IgG monoclonal antibody which is processed simultaneously with the immune sera samples. The secondary anti-OVA IgG immune response is determined from the end-point titers as follows: the absorbance due to antigen-specific binding is plotted as a function of the logarithm of the serum dilution, and the end-point titer is estimated from the serum dilution yielding an absorbance of 0.25. End-point titers of 3.6 or less are obtained with sera from immunizations without an adjuvant, and end point titers near or higher than 5.0 with different adjuvants. Dialyzed *Quillaja saponaria* Molina saponins at an adjuvant does of 10 µg increases titers by almost 2 orders of magnitude compared to OVA in PBS. The primary immune response from immunizations with OVA plus desacylated quillajasaponins yields IgG levels lower that those elicited by OVA in PBS.

A conjugate as prepared in Example 3 was tested for adjuvanticity at doses of 10, 50 and 250 µg. The conjugate demonstrated a good dose-dependent adjuvant effect on the production of anti-OVA IgG during the primary and secondary immune response (FIGS. 3, 4, 5, 6). This conjugate yields end-point titers approaching those induced by quillaja saponin, i.e. 4.70 to 5.85. As opposed to quillajasaponins, this conjugate preferentially stimulates the production of IgG1. No negative side effects were observed with this conjugate in the dose range tested: 10 to 250 µg.

EXAMPLE 9

Testing for Adjuvant Effect on T-Cell Immunity Using OVA as Antigen

In many viral vaccines, and likely in cancer vaccines, the adjuvant used with the protein antigens should elicit a strong specific cell-mediated immunity (CMI) or T-cell immune response with production of cytotoxic T lymphocytes (CTL). Presently, quillajasaponins are the only adjuvants capable of eliciting T-cell immunity (Newman et al., *J. Immuno*. 148:2357 (1992)). The other adjuvants, including muramyl dipeptides, glucans, immune modulators such as IL-2, and others, are only capable of stimulating a humoral immune response against exogenous proteins (Cod, J. C., and Coulter, A. R., *Vaccine* 15:248 (1997)), which would be of little value in the case of cancer and some viral vaccines. Desacylation of quillajasaponins results in non-toxic products, but, with no adjuvant activity, as measured by antibody production (Kensil et al., *Vaccines* 92:35 (1992)) and CTL response (Kensil et al., in *Saponins Used in Traditional and Modern Medicine*; Kamasaki, K., Waller, G. R., Eds. Plenum, N.Y., in press). Because of their stimulation of humoral and T-cell immunity, as well as negligible toxicity, the semi-synthetic analogs or saponin-lipophile conjugates of the present invention are suitable for the preparation of viral or cancer vaccines. T-cell immunity induced by these adjuvants can be assayed in vitro by (i) blast transformation, which measures the proliferation response of sensitized T cells to antigens, or (ii) measurement of the enhancement of CTL priming to a protein antigen (dodecylamine conjugated to desacylated quillaja saponin).

Figure 7:
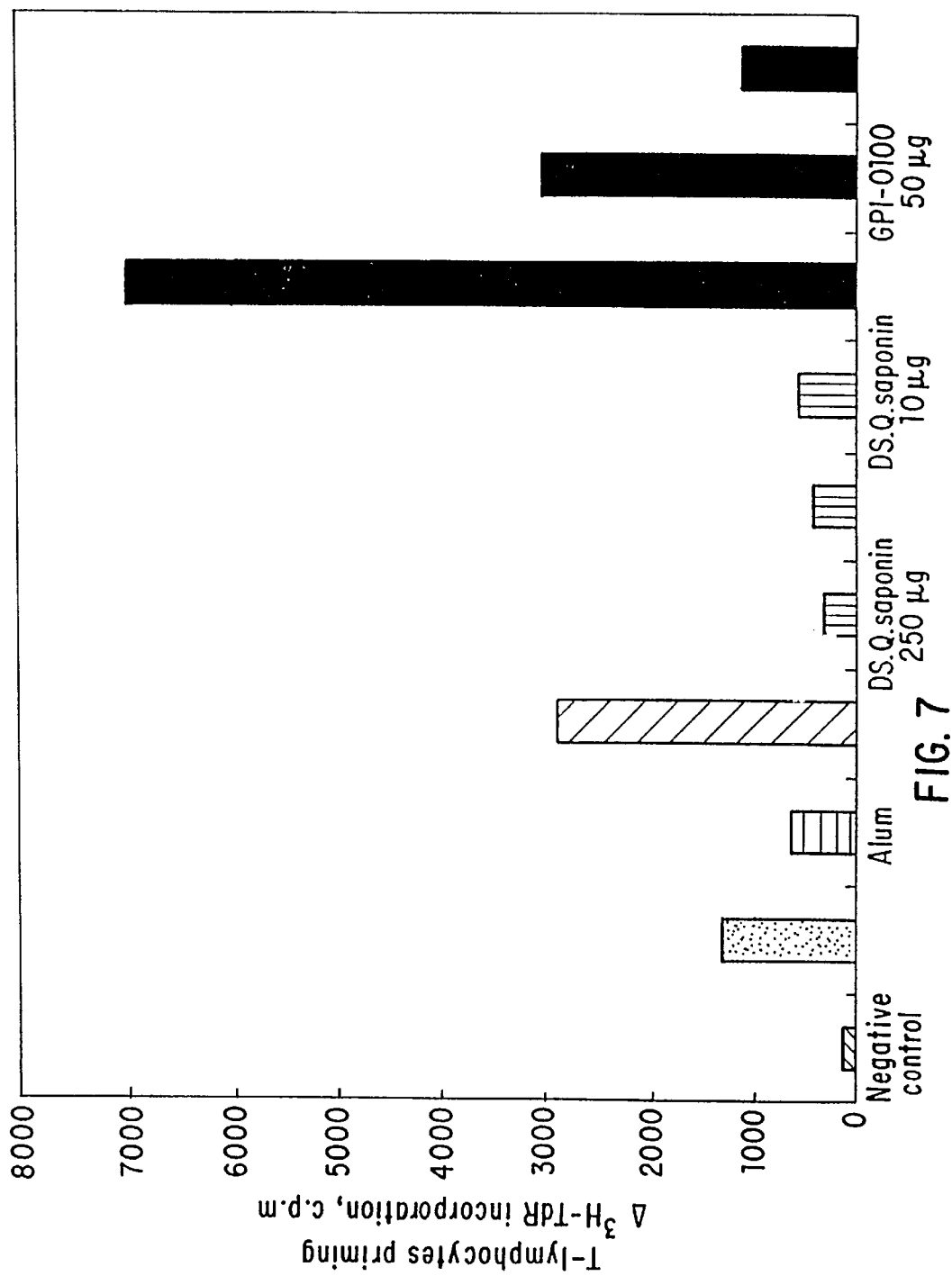
FIG. 7 demonstrates the comparison of the in vitro proliferative responses induced in T-lymphocytes isolated from mice immunized twice with OVA alone, or in the presence of alum, quillaja saponin, differing doses of desacylated quillaja saponin, and quillaja saponin-lipophile conjugate of the present invention (GPI-0100). The degree of priming was determined by stimulating the spleenocytes with either 2 or 10 μg of OVA and measuring the incremental changes in $^3$H-thymidine incorporation (Δ $^3$H-TdR incorporation, c.p.m.).

The adjuvant effect on T-cell immunity is measured by a cell proliferation assay according to the following protocol. Six to eight week old female C57BL/6 mice are immunized twice subcutaneously with the following formulation: 20 µg OVA (Sigma) and an adjuvant of the present invention or desacylated quillajasaponins (at doses ranging from 10–250 µg) or quillajasaponins (at a dose of 10 µg) in 200 µl PBS. The two immunizations are given at two week intervals. Control mice are injected with either PBS or PBS with OVA, plus 200 µg of aluminum hydroxide. Two weeks after the second immunization, the spleens are removed and disrupted by extruding through a nylon mesh. The cells are washed and resuspended in RPMI 1640 medium with 10% heat-inactivated fetal calf serum, 100 µg/ml streptomycin, 100 µg/ml penicillin, 10 µg/ml gentamycin, 2 mM L-glutamine, and 2×10−5 M 2-mercaptoethanol. Two×10$^5$ spleen cells are dispensed in 100 µl volumes into microtiter plate wells, and cultured in triplicate with either medium alone (for use as background), 3 µg/ml Concavalin A, 2 µg/ml of OVA or 10 µg/ml of OVA. After 72 h. in culture, the cells are pulsed with 1 µCi of tritiated thymidine ($^3$H-thymidine, Amersham International) for 16 h. and harvested using a Skatron (Sterling, Va.) semi-automated harvester. The amount of label that is incorporated into cellular DNA is determined by liquid scintillation counting. Cell proliferation is expressed as the differential (Δ cpm) in $^3$H-thymidine incorporated between the spleenocytes stimulated with either 2 or 10 µg of OVA in vitro. As determined from the $^3$H-thymidine incorporation in the presence of OVA, T-lymphocytes from mice immunized with OVA plus quillajasaponins show a proliferative response that is significantly higher than that observed with alum. T-cells from mice immunized with OVA and different doses of desacylated quillajasaponins showed a proliferative response that was lower than that observed with alum. T-lymphocytes from mice immunized with OVA plus 50 or 250 µg of saponin conjugate, showed an in vitro proliferative response (Δ c.p.m.) that was similar to or considerably higher than that observed with quillajasaponins (FIG. 7).

EXAMPLE 10
Testing for Adjuvant Effect on the Production of Antigen Specific Cytotoxic T Lymphocytes (CTLs)

Spleen cells were added to 24-well plates containing $2\times10^6$ cells in 1 ml of complete medium plus denatured OVA (dOVA). To generate effector cells, the spleen cell were incubated in vitro with X-ray irradiated E.G7-OVA cells for six days prior at 37° C. Cells were harvested and washed to yield the effector (E) population. Target cells (T) consisted of EL-4 and E.G7-OVA. EL-4 cells were grown in high glucose Dulbecco's Modified Eagle Medium containing 10% horse serum. E.G7-OVA cells were grown in RPMI 1640 medium supplemented with 10% FBS, high glucose, Na pyruvate, β-mercaptoethanol and G418. Target cells were labeled for 1 hour with 300 μCi of $^{51}$Cr-labeled $NaCrO_4$ and washed. Effector and target cells were added in various E:T ratios to Costar round-bottom 96-well microtiter plates (each well containing $1\times10^4$ target cells), centrifuged for about 30 seconds at 200×g and incubated at 37° C. in a humidified 5% $CO_2$ incubator. After 4 hours cells were harvested with th Skatron Supernatant Collection System and the supernatant radioactivity was counted in a gamma counter. Control for the CTL assays consisted of target cells lysed with 2% Triton X-100 (maximum release) and target cell incubated with medium only (spontaneous release). The percent lysis for each E:T ratio was calculated by the formula: % lysis=[(experimental cpm−spontaneous cpm)/(maximum cpm−spontaneous cpm)]×100.

EXAMPLE 11
Addition of Biotin to the Carboxyl Group of Glucuronic Acid

Figure 8:
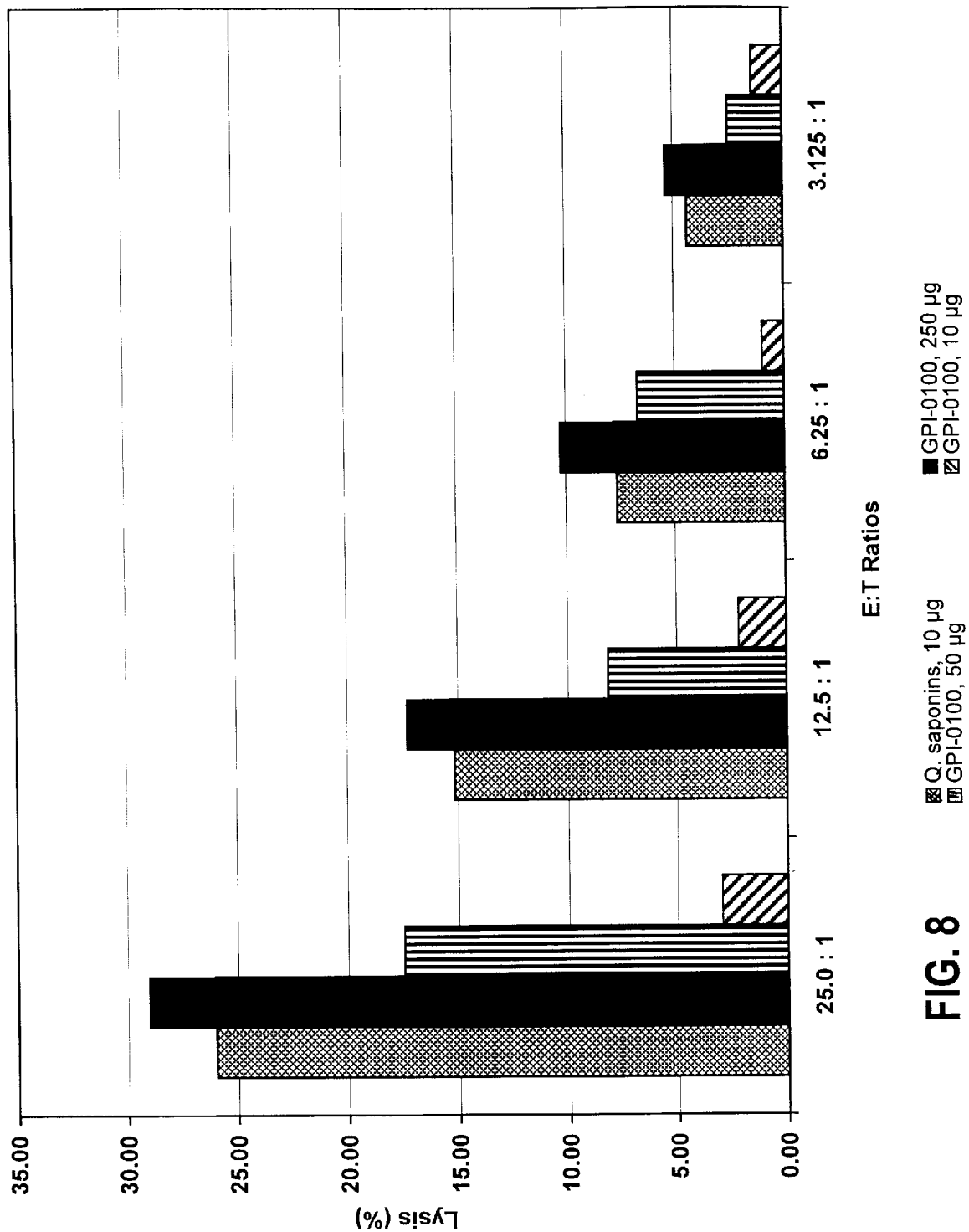
FIG. 8 demonstrates a comparison of the stimulation of cytotoxic T-lymphocytes (CTLs) in mice immunized three times with denatured OVA plus quillaja saponin or a quillaja saponinlipophile conjugate of the present invention (GPI-0100). To generate effector cells, spleen cells were incubated in vitro with X-ray irradiated E.G7-OVA cells for six days prior to the $^{51}$Cr-release assay. The assay was carried out using EL-4 cells and E.G7-OVA cells (derived from EL-4 by transfection with the OVA gene) as targets. After a 4 hour incubation of the effector cells with the target cells, the cells were harvested and the radioactivity in the supernatant measured in a gamma counter. The percent of specific lysis was calculated using the $^{51}$Cr released from $^{51}$Cr-labeled target cells lysed with 2% Triton X-100 as 100% lysis.

A $C_2$–$C_6$ aliphatic diamine is added to the carboxyl group of the glucuronic acid residue of saponins from gypsophila, saponaria, or the desacylated quillajasaponins using the carbodimide method described in Example2. Addition of the biotin group is achieved by linking an active ester derivative (S—NHS) of biotin (Pierce) to the free amino group of the $C_2$–$C_6$ aliphatic diamine derivative of the saponin. The results demonstrating a CTL response for GPI-100 are depicted in FIG. 8.

EXAMPLE 12
Testing for Binding of Biotinylated Saponins to T-cells

Lymphoblasts, white blood cells, or cultured cells, are incubated in PBS at 37° C. with biotinylated saponin, with or without Na cyanoborohydride. After incubation, the cells are washed with PBS containing BSA, and collected by centrifugation. To the washed and re-suspended cells, a FITC-conjugated avidin or strepavidin is added and the mixture is incubated. The cells are washed with PBS containing 10% fetal calf serum, and the samples are analyzed by fluorescence microscopy or by flow cytometry. Cells incubated with biotinylated saponin without cyanoborohydride are used to provide a background measure. Cells incubated in the presence of cyanoborohydride provide a measure of the T-cells with CD28 cell-surface-receptors which are capable of binding imine-forming saponins (including those that are biotinylated). These cells are susceptible to co-stimulation by B7.1 and thus to activation.

EXAMPLE 13
Feline Leukemia Virus Vaccine

To 20–50 μg of a recombinant antigen from feline leukemia virus (FeLV) suspended with 0.2 mg of alum in 0.8 ml of sterile phosphate buffered saline, pH 7.2, add 0.2 ml of a solution containing 0.5 mg of GPI-0100 dissolved in PBS. Mix and store at 4° C.

EXAMPLE 14
HSV-1 Glycoprotein D Vaccine

To 20–80 μg of HSV-1 glycoprotein D, expressed in insect cells using the baculovirus vector and dissolved in 0.8 ml of PBS containing 10 to 40 mg of isomannide monooleate orpolysorbate, add 0.2 ml of a solution containing 0.5 mg of GPI-0100 dissolved in PBS. Mix and store at 4° C.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

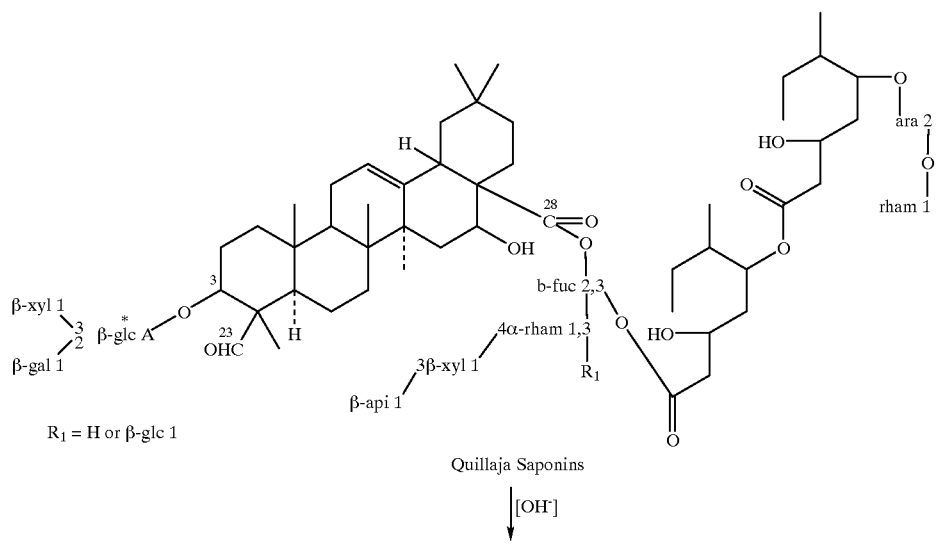

Scheme 1

Quillaja Saponins

-continued

β-xyl 1
     \3
      >2  β-glc A*
β-gal 1        23
              OHC

4α-rham 1,3
              3β-xyl 1
       β-api 1                  R₁

R₁ = H or β-glc 1

Quillaja Desacylated Saponins

Scheme 2
Preparation of Desacylated Quillaja Saponins

Quillaja bark
↓ H₂O extraction

Filter H₂O extract
dry in vacuo
↓

Dissolve in H₂O, adjust pH < 4.0
Dyalized against H₂O
↓

Dry dialysate in vacuo and
extract materials with MeOH → Reflux saponins for 1 hour in
(MetOH-soluble saponins)          6% NaHCO₃ in 50% MetOH
                                          ↓

Desacylsaponins
DS-1 and DS-2 plus   ← Neutralize w/Dowex 50W-X8,
free acyl groups         filter and evaporate in vacuo
↓

Elute w/CHCl₃ ——— DS-1
Silica gel       MeOH—AcOH—H₂O
chromatography                    ↘
                    ↓              DS-2
              Acyl groups and sugars
                   (disgard)

Scheme 3
Squarroside A
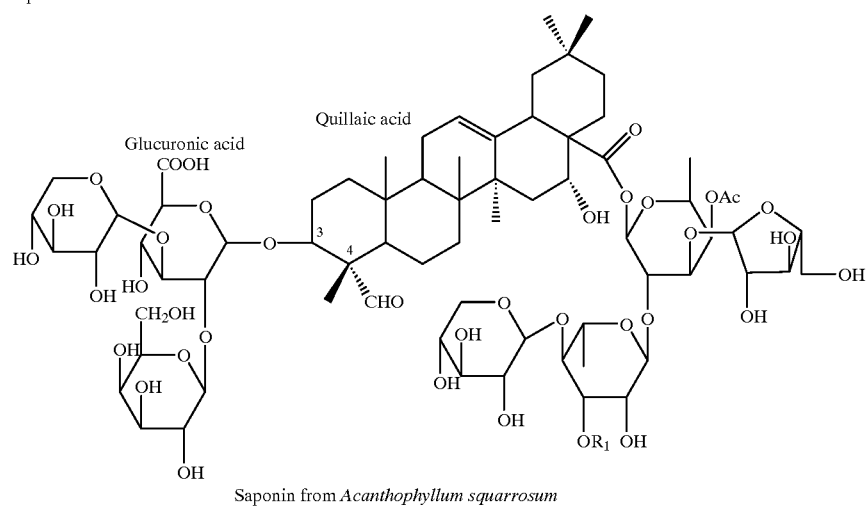
Saponin from *Acanthophyllum squarrosum*
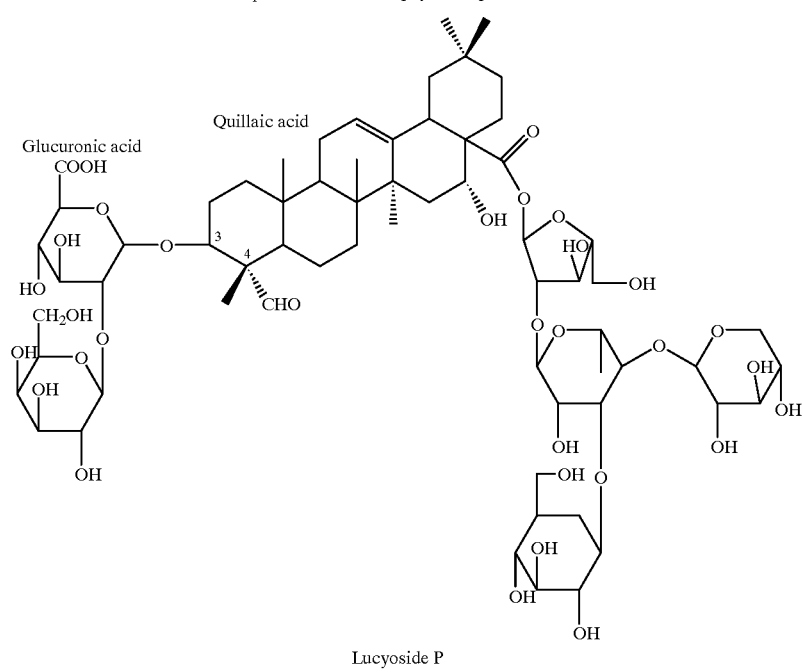
Lucyoside P
Scheme 4
Synthesis of hydrophobic-hydrophilic side-chain
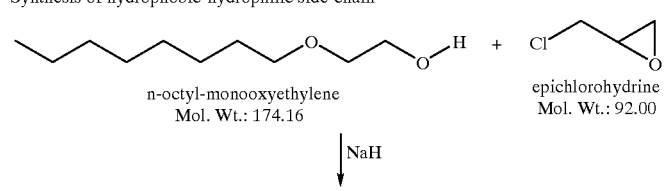

-continued epoxylated n-octyl-monooxyethylene (11)
Mol. Wt.: 230.19

\+ cysteine
Mol. Wt.: 121.15

↓ n-octyl-monooxyethylene-cysteine (12)
Mol. Wt.: 351.34

Scheme 5
Activation of Glucuronic acid in DS-Quillajasaponin

NHS
Mol. Wt.: 115.03

\+

Glucuronic acid

↓ [DCC] M.W. = 206.33

-continued

NHS-glucuronate ester intermediate

Scheme 6
Addition of the hydrophobic-hydrophilic side-chain to DS-saponin n-octyl-monooxyethelene-cysteine (12)
Mol. Wt.: 351.21

\+

NHS-glucuronate ester intermediate (13)

↓

Modified DS-Quillajasaponin (14)

Scheme 7
Synthesis of hydrophobic-hydrophilic side-chain n-octyl-monooxyethylene
Mol. Wt.: 174.16

+ epichlorohydrine
Mol. Wt.: 92.00

Mol. Wt.: 230.19

+ ethylenediamine
Mol. Wt.: 116.13 side-chain w/ethylenediamine
Mol. Wt.: 332.30

Scheme 8
Addition of the hydrophobic-hydrophilic side-chain to DS-saponin

Hydrophobic/hydrophilic side-chain*
Mol. Wt.: 332.30

+ NHS-glucuronate ester intermediate

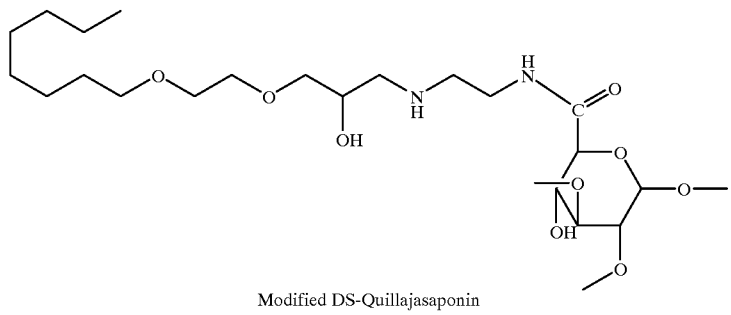

Modified DS-Quillajasaponin

*w/ethylenediamine

What is claimed is:

1. A vaccine for human or veterinary use, comprising:
   (a) one or more bacterial, viral, protozoal or tumor associated antigens, and
   (b) one or more saponin-lipophile conjugates, in which
       (1) a non-acylated or deacylated triterpene saponin having a 3-O-glucuronic acid residue is covalently attached, either directly or via a linking moiety, to:
       (2) a compound having a lipophilic domain,
           wherein (1) is attached to (2) via the carboxyl carbon atom present on the 3-O-glucuronic acid residue of the triterpene saponin.

2. The vaccine of claim 1, wherein said saponin-lipophile conjugate is a conjugate of
   (1) Quillaja desacylsaponin, having a 3-glucuronic acid residue, a triterpene aglycone core structure, branched sugar chains attached to positions 3 and 28, and an aldehyde group at position 4, and lacking an acyloyl group on a saccharide at the 28-position of the triterpene aglycone; and
   (2) a lipophilic moiety; wherein said saponin and said lipophilic moiety are covalently attached to one another, either directly or through a linker group, and wherein said direct attachment or attachment to said linker occurs through a covalent bond between the carboxyl carbon of said 3-glucuronic acid residue, and a functional group on the lipophilic residue or linker group.

3. The vaccine of claim 2, wherein said lipophilic moiety of said saponin-lipophile conjugate is a residue of a compound selected from the group consisting of a fatty acid, terpenoid, aliphatic amine, aliphatic alcohol, aliphatic mercaptan, mono- or poly-$C_2$–$C_4$ alkyleneoxy derivative of a fatty acid, mono- or poly-$C_2$–$C_4$ alkyleneoxy derivative of a fatty alcohol, glycosyl-fatty acid, glycolipid, phospholipid, a monoacylglycerol, and a diacylglycerol.

4. The vaccine of claim 3, wherein said lipophilic moiety of said saponin-lipophile conjugate is a residue of a compound selected from the group consisting of aliphatic amine, aliphatic alcohol, and aliphatic mercaptan, each having from 6 to 20 carbon atoms.

5. The vaccine of claim 4, wherein said lipophilic moiety is a residue of nonylamine or dodecylamine.

6. The vaccine of claim 3, wherein said lipophilic moiety of said saponin-lipophile conjugate is a residue of a $C_{14}$–$C_{24}$ fatty acid.

7. The vaccine of claim 6, wherein said fatty acid is selected from the group consisting of lauric, myristic, palmitic, stearic, arachidic, behenic, lignoceric, palmitoleic, oleic, linoleic, linolenic and arachidonic acids.

8. The vaccine of claim 3, wherein said lipophile moiety of said saponin-lipophile conjugate is a residue of a terpenoid.

9. The vaccine of claim 3, wherein said lipophilic moiety of said saponin-lipophile conjugate is a phosphoglyceride, mono-acylglycerol or di-acylglycerol.

10. The of claim 3, wherein said lipophilic moiety of said saponin-lipophile conjugate is a residue of a glycosyl-fatty acid or a glycolipid.

11. The vaccine of claim 1, wherein said one or more antigens are bacterial antigens.

12. The vaccine of claim 11, wherein said bacterial antigens are antigens associated with a bacterium selected from the group consisting of *Helicobacter pylori, Chlamydia pneumoniae, Chlamydia trachomatis, Ureaplasma urealyticum, Mycoplasma pneumoniae,* Staphylococcus spp., *Staphylococcus aureus,* Streptococcus spp., *Streptococcus pyogenes, Streptococcus pneumoniae, Streptococcus viridans, Enterococcus faecalis, Neisseria meningitidis, Neisseria gonorrhoeae, Bacillus anthracis,* Salmonella spp., *Salmonella typhi, Vibrio cholera, Pasteurella pestis, Pseudomonas aeruginosa,* Campylobacter spp., *Campylobacter jejuni,* Clostridium spp., *Clostridium difficile,* Mycobacterium spp., *Mycobacterium tuberculosis,* Treponema spp., Borrelia spp., *Borrelia burgdorferi,* Leptospria spp., *Hemophilus ducreyi, Corynebacterium diphtheria, Bordetella pertussis, Bordetella parapertussis, Bordetella bronchiseptica, hemophilus influenza, Escherichia coli,* Shigella spp., Erlichia spp., Rickettsia spp. and combinations thereof.

13. The vaccine of claim 1, wherein said one or more antigens are viral-associated antigens.

14. The vaccine of claim 13, wherein said viral-associated antigens are antigens associated with a virus selected from the group consisting of Influenza viruses, Parainfluenza viruses, Mumps virus, Adenoviruses, Respiratory syncytial virus, Epstein-Barr virus, Rhinoviruses, Polioviruses, Coxsackieviruses, Echo viruses, Rubeola virus, Rubella virus, Varicell-zoster virus, Herpes viruses, Herpes simplex virus, Parvoviruses, Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus, Foot and mouth disease virus, and combinations thereof.

15. The vaccine of claim 1, wherein said one or more antigens are tumor-associated antigens.

16. The vaccine of claim 15, wherein said tumor-associated antigens are antigens selected from the group consisting of killed tumor cells and lysates thereof, MAGE- 1, MAGE-3 and peptide fragments thereof; Human chorionic gonadotropin and peptide fragments thereof; Carcinoembryonic antigen and peptide fragments thereof, Alpha fetoprotein and peptide fragments thereof; Pancreatic oncofetal antigen and peptide fragments thereof; MUC-1 and peptide fragments thereof, CA 125, CA 15-3, CA 19-9, CA 549, CA 195 and peptide fragments thereof; Prostate-specific antigens and peptide fragments thereof; Prostate-specific membrane antigen and peptide fragments thereof; Squamous cell carcinoma antigen and peptide fragments thereof; Ovarian cancer antigen and peptide fragments thereof; Pancreas cancer associated antigen and peptide fragments thereof; Her1/neu and peptide fragments thereof; gp-100 and peptide fragments thereof; mutant K-ras proteins and peptide fragments thereof; mutant p53 and peptide fragments thereof; truncated epidermal growth factor receptor, chimeric protein p210$^{BCR-ABL}$; and mixtures thereof.

17. The vaccine of claim 1, wherein said one or more antigens are native, recombinant or synthetic.

18. The vaccine of claim 1, wherein said one or more antigens are employed, either free, non-covalently associated, or conjugated covalently to a pharmaceutically acceptable carrier.

19. The vaccine of claim 1, wherein said saponin-lipophile conjugate is represented by Formula II:

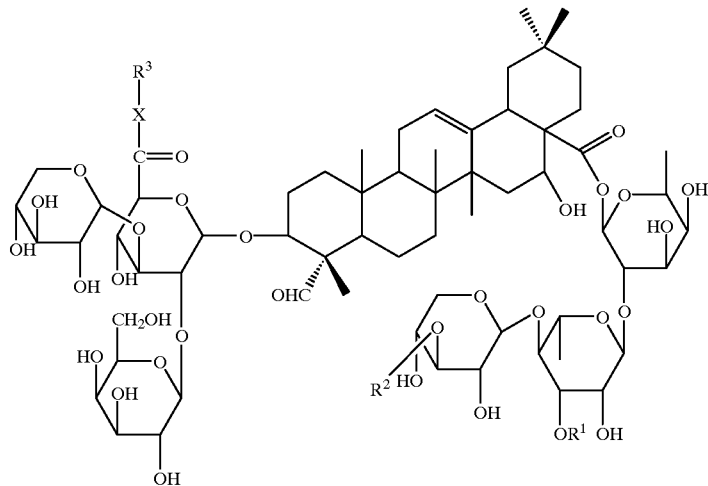

or a pharmaceutically acceptable salt thereof; wherein
R$^1$ is glucose or hydrogen; R$^2$ is apiose or xylose; X is S, O, NH, NR$^4$ or a linking group; R$^3$ is a lipophilic moiety; and R$^4$ is lower alkyl or a lipophilic moiety.

20. The vaccine of claim 19, wherein X is a linking group, and said linking group is a bifunctional molecule.

21. The vaccine of claim 19, wherein X is a linking group selected from the group consisting of —NH—CH$_2$—CH$_2$—NH—, —NH—CH(COOH)—CH$_2$—NH—, —NH—CH$_2$—CH(COOH)—NH—, —NH—CH$_2$—CH$_2$—CH$_2$—NH—, —O—(CH$_2$)$_r$—NH—, —S—(CH$_2$)$_r$—NH—, —S—(CH$_2$)$_r$—C(O)—, —NH—CH$_2$—C(O)—, —O—CH$_2$—CH$_2$—O—CH$_2$—CH$_2$—O—, —NH—NH—C(O)—CH$_2$—, —NH —C(CH$_3$)$_2$—C(O)—, and —NH—NH—C(O)—(CH$_2$)$_r$—C(O)—NH—N=, where r is from 2–5.

22. The vaccine of claim 19, wherein R$^3$ is selected from the group consisting of a C$_4$–C$_{30}$ straight or branched chain alkyl group, and a C$_4$–C$_{30}$ straight or branched chain alkenyl group; either of which is optionally substituted by one or more of hydroxy, C$_1$–C$_6$ alkoxy, or mercapto, and is optionally interrupted by one or more components selected from the group consisting of NH, N(R$^{10}$), S, O, sulfinyl and sulfonyl groups, where R$^{10}$ is C$_{1-6}$alkyl; and R$^4$ is C$_1$–C$_3$ alkyl, or is the same as R$^3$.

23. The vaccine of claim 22, wherein X is NH or NR$^4$, where R$^4$ is C$_1$–C$_3$ alkyl, or is the same as R$^3$.

24. The vaccine of claim 23, wherein X is NH, and R$^3$ is nonyl or dodecyl.

25. The vaccine of claim 19, wherein the combination of —X—R$^3$ is a residue of a compound selected from the group consisting of a fatty acid, terpenoid, aliphatic amine, aliphatic alcohol, aliphatic mercaptan, mono- or poly-C$_2$–C$_4$ alkyleneoxy derivative of a fatty acid, mono- or poly-C$_2$–C$_4$ alkyleneoxy derivative of a fatty alcohol, glycosyl-fatty acid, glycolipid, phospholipid, a monoacylglycerol, and a diacylglycerol.

26. The vaccine of claim 19, wherein the combination of —X—R$^3$ is a residue of an aliphatic amine.

27. The vaccine of claim 19, further comprising a pharmaceutically acceptable carrier or diluent.

28. A method of potentiating an immune response to an antigen, comprising administering to a subject a vaccine of claim 1 in an effective amount to potentiate the immune response of said subject to said antigen.

29. A method of vaccinating a subject, comprising administering a vaccine of claim 1 to said subject.

30. A method of potentiating an immune response to an antigen, comprising administering to a subject a vaccine of claim 2 in an effective amount to potentiate the immune response of said subject to said antigen.

31. A method of vaccinating a subject, comprising administering a vaccine of claim 2 to said subject.

32. A method of potentiating an immune response to an antigen, comprising administering to a subject a vaccine of claim 5 in an effective amount to potentiate the immune response of said subject to said antigen.

33. A method of vaccinating a subject, comprising administering a vaccine of claim 5 to said subject.

34. A method of potentiating an immune response to an antigen, comprising administering to a subject a vaccine of claim 19 in an effective amount to potentiate the immune response of said subject to said antigen.

35. A method of vaccinating a subject, comprising administering a vaccine of claim 19 to said subject.

36. A method of potentiating an immune response to an antigen, comprising administering to a subject a vaccine of claim 24 in an effective amount to potentiate the immune response of said subject to said antigen.

37. A method of vaccinating a subject, comprising administering a vaccine of claim 24 to said subject.

* * * * *